United States Patent
Paul et al.

(10) Patent No.: US 12,383,736 B2
(45) Date of Patent: Aug. 12, 2025

(54) CATHETER SYSTEMS

(71) Applicant: St. Jude Medical, Atrial Fibrillation Division, Inc., St. Paul, MN (US)

(72) Inventors: Saurav Paul, Shoreview, MN (US); Troy T. Tegg, Elk River, MN (US); Israel A. Byrd, Richfield, MN (US); Riki Thao, Little Canada, MN (US); Harry A. Puryear, Shoreview, MN (US); Linda Nemec, Andover, MN (US)

(73) Assignee: St. Jude Medical, Atrial Fibrillation Division, Inc., St. Paul, MN (US)

( * ) Notice: Subject to any disclaimer, the term of this patent is extended or adjusted under 35 U.S.C. 154(b) by 0 days.

(21) Appl. No.: 18/754,711

(22) Filed: Jun. 26, 2024

(65) Prior Publication Data

US 2024/0342469 A1    Oct. 17, 2024

Related U.S. Application Data

(63) Continuation of application No. 17/227,924, filed on Apr. 12, 2021, which is a continuation of application (Continued)

(51) Int. Cl.
*A61B 18/14* (2006.01)
*A61N 1/32* (2006.01)
*A61B 18/00* (2006.01)

(52) U.S. Cl.
CPC ............ *A61N 1/327* (2013.01); *A61B 18/14* (2013.01); *A61B 2018/0016* (2013.01)

(58) Field of Classification Search
CPC ...... A61B 2018/00577; A61B 18/1492; A61B 2018/00613; A61B 2018/00267;
(Continued)

(56) References Cited

U.S. PATENT DOCUMENTS 5,673,695 A * 10/1997 McGee ............... A61B 5/6855
607/148
6,009,347 A    12/1999 Hofmann
(Continued)

FOREIGN PATENT DOCUMENTS

WO   2007067937 A2   6/2007
WO   2009079626 A1   6/2009
(Continued)

OTHER PUBLICATIONS

Abstract of Liu et al., "An Optical Thermometer for Direct Measurement of Cell Temperature in the Beckman Instruments XL-A Analytical Ultracentrifuge", Analytical Biochemistry, vol. 224, Issue 1, Jan. 1995, pp. 199-202.
(Continued)

*Primary Examiner* — Michael F Peffley
*Assistant Examiner* — Amanda L Zink
(74) *Attorney, Agent, or Firm* — Armstrong Teasdale LLP

(57) ABSTRACT

Catheter systems include direction-sensitive, multi-polar tip electrode assemblies for electroporation-mediated therapy, electroporation-induced primary necrosis therapy and electric field-induced apoptosis therapy, including configurations for producing narrow, linear lesions as well as distributed, wide area lesions. A monitoring system for electroporation therapy includes a mechanism for delivering electrochromic dyes to a tissue site as well as a fiber optic arrangement to optically monitor the progress of the therapy as well as to confirm success post-therapy. A fiber optic temperature sensing electrode catheter includes a tip electrode having a cavity whose inner surface is impregnated or coated with thermochromic/thermotropic material that changes color with changes in temperature. An optic fiber/detector arrangement monitors the thermochromic or thermotropic materials, acquiring a light signal and generating
(Continued)

an output signal indicative of the spectrum of the light signal. An analyzer determines an electrode temperature based on the detector output and predetermined spectrum versus temperature calibration data.

18 Claims, 11 Drawing Sheets

Related U.S. Application Data

No. 15/931,240, filed on May 13, 2020, now Pat. No. 11,000,684, which is a continuation of application No. 15/064,664, filed on Mar. 9, 2016, now Pat. No. 10,688,300, which is a continuation of application No. 12/874,788, filed on Sep. 2, 2010, now Pat. No. 9,289,606.

(58) Field of Classification Search
CPC ........... A61B 2018/00702; A61B 2018/00642; A61B 2018/1467; A61B 18/1206; A61B 2018/00351; A61B 2018/00404; A61B 2018/00375; A61B 2018/126; A61B 2018/0016; A61B 2018/1407
See application file for complete search history.

(56) References Cited

U.S. PATENT DOCUMENTS

| | | | |
|---|---|---|---|
| 6,055,453 A * | 4/2000 | Hofmann | A61P 35/00 607/116 |
| 6,152,882 A | 11/2000 | Prutchi | |
| 6,241,724 B1 | 6/2001 | Fleischman et al. | |
| 6,292,695 B1 * | 9/2001 | Webster, Jr. | A61N 1/0563 607/148 |
| 6,391,024 B1 * | 5/2002 | Sun | A61B 18/1206 606/49 |
| 7,195,628 B2 | 3/2007 | Falkenberg | |
| 7,263,397 B2 | 8/2007 | Hauck et al. | |
| 7,326,204 B2 | 2/2008 | Paul et al. | |
| 7,419,489 B2 | 9/2008 | Vanney et al. | |
| 7,591,816 B2 | 9/2009 | Wang et al. | |
| 8,043,288 B2 | 10/2011 | Dando et al. | |
| 8,226,648 B2 | 7/2012 | Paul et al. | |
| 8,295,902 B2 * | 10/2012 | Salahieh | A61B 18/1492 606/41 |
| 8,403,925 B2 | 3/2013 | Miller et al. | |
| 8,728,077 B2 | 5/2014 | Paul et al. | |
| 9,289,606 B2 | 3/2016 | Paul et al. | |
| 10,688,300 B2 | 6/2020 | Paul et al. | |
| 11,000,684 B2 | 5/2021 | Paul et al. | |
| 2002/0123749 A1 * | 9/2002 | Jain | A61B 18/1492 606/41 |
| 2003/0130711 A1 * | 7/2003 | Pearson | A61B 18/1477 607/101 |
| 2005/0049542 A1 | 3/2005 | Sigg et al. | |
| 2006/0111708 A1 | 5/2006 | Vanney et al. | |
| 2006/0287650 A1 | 12/2006 | Cao et al. | |
| 2007/0005053 A1 | 1/2007 | Dando | |
| 2007/0106291 A1 | 5/2007 | Thao et al. | |
| 2008/0091192 A1 | 4/2008 | Paul et al. | |
| 2008/0140072 A1 | 6/2008 | Stangenes et al. | |
| 2008/0161790 A1 | 7/2008 | Dando et al. | |
| 2008/0275465 A1 | 11/2008 | Paul et al. | |
| 2009/0076336 A1 | 3/2009 | Mazar et al. | |
| 2009/0171187 A1 | 7/2009 | Gerhart et al. | |
| 2009/0171331 A1 | 7/2009 | Paul et al. | |
| 2009/0171337 A1 | 7/2009 | Paul et al. | |
| 2009/0171343 A1 | 7/2009 | Paul et al. | |
| 2010/0069921 A1 | 3/2010 | Miller et al. | |
| 2010/0204560 A1 * | 8/2010 | Salahieh | A61B 5/01 606/41 |
| 2012/0296329 A1 * | 11/2012 | Ng | A61B 18/1492 606/41 |

FOREIGN PATENT DOCUMENTS

| | | |
|---|---|---|
| WO | 2009124220 A2 | 10/2009 |
| WO | 2010056771 A1 | 5/2010 |

OTHER PUBLICATIONS

Partial European Search Report, EP11175829.8, Nov. 29, 2011, 7 pages.
Supplemental European Search Report, EP11175829.8, Mar. 19, 2012, 10 pages.

* cited by examiner

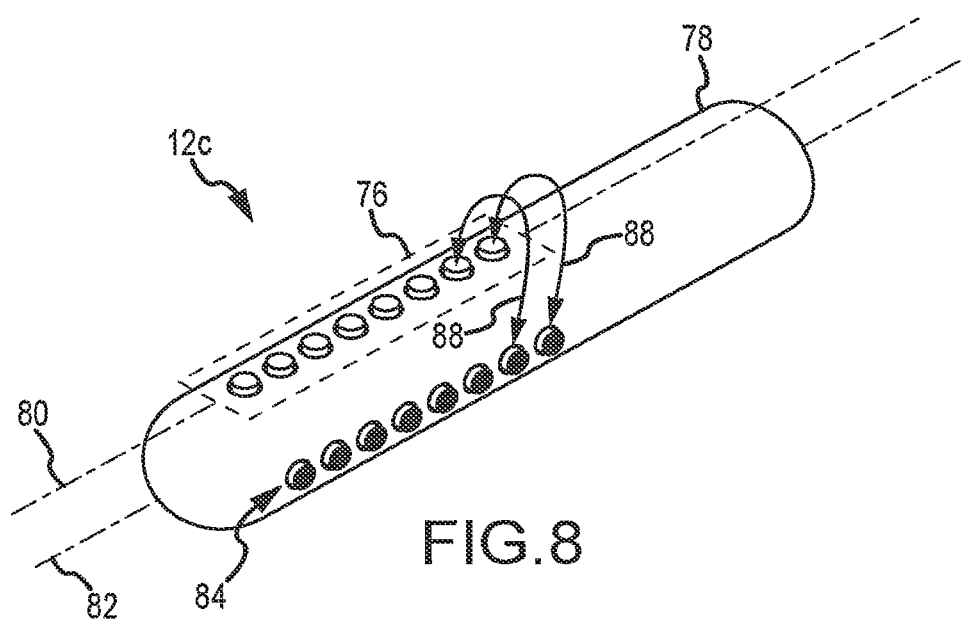
FIG.8
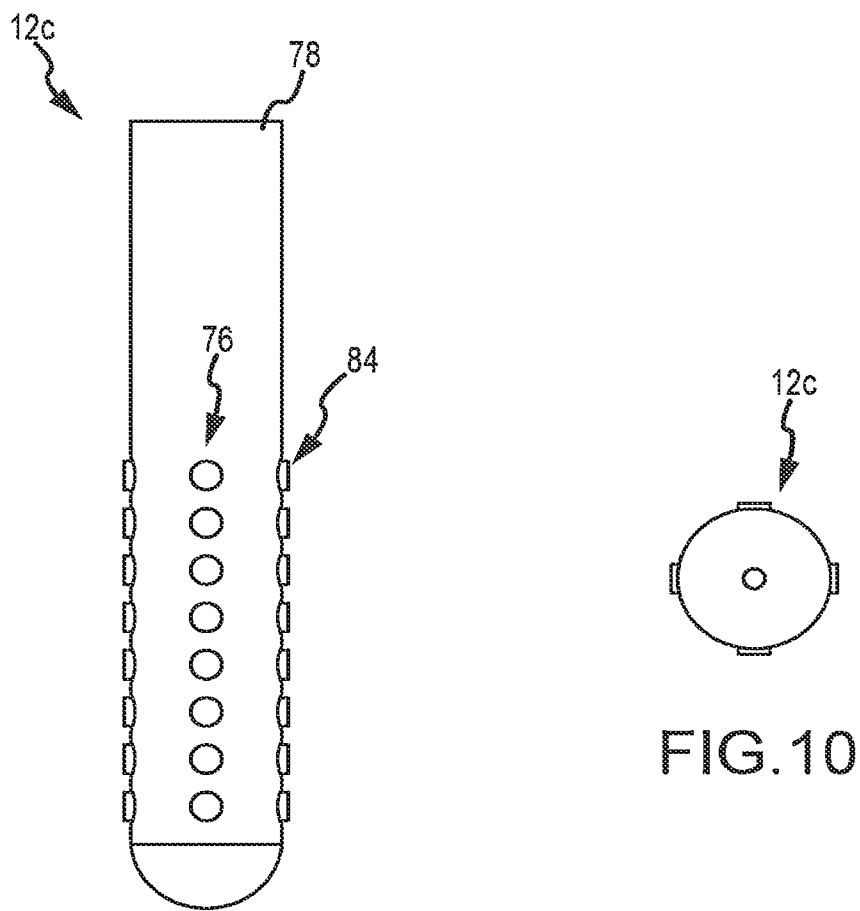
FIG.9
FIG.10

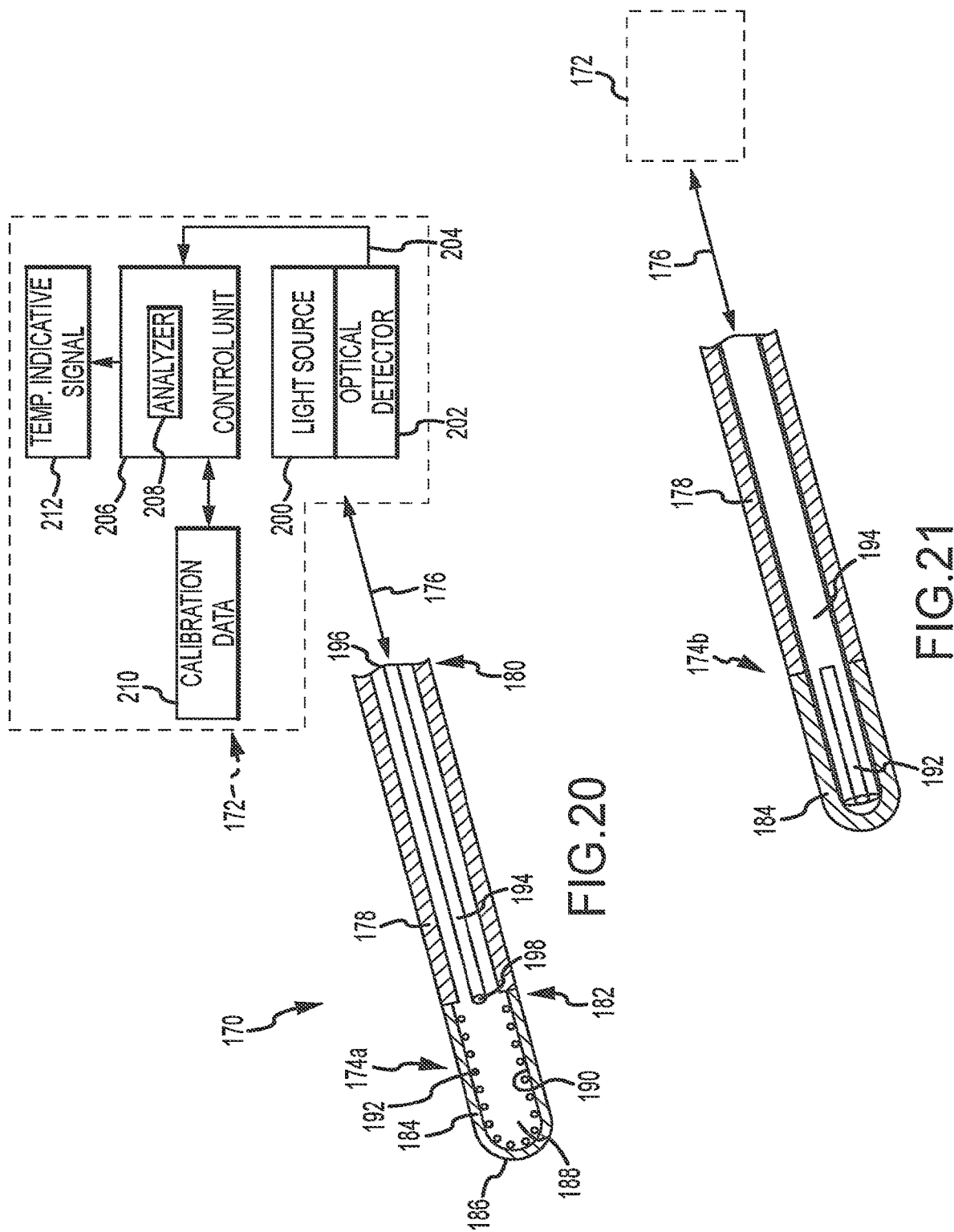

CATHETER SYSTEMS

CROSS-REFERENCE TO RELATED APPLICATIONS

This application is a continuation of U.S. application Ser. No. 17/227,924, filed 12 Apr. 2021 (the '924 application), now pending, which is a continuation of U.S. application Ser. No. 15/931,240, filed 13 May 2020 (the '240 application), now U.S. Pat. No. 11,000,684, which is a continuation of U.S. application Ser. No. 15/064,664, filed 9 Mar. 2016 (the '664 application), now U.S. Pat. No. 10,688,300, which is a continuation of U.S. application Ser. No. 12/874,788, filed 2 Sep. 2010 (the '788 application), now U.S. Pat. No. 9,289,606. The '924 application, the '240 application, the '664 application and the '788 application are all hereby incorporated by reference as though fully set forth herein.

BACKGROUND OF THE INVENTION a. Field of the Invention

The instant invention relates generally to catheter systems.

b. Background Art

It is generally known that ablation therapy may be used to treat various conditions afflicting the human anatomy. One such condition that ablation therapy finds a particular application is in the treatment of atrial arrhythmias, for example. When tissue is ablated, or at least subjected to ablative energy generated by an ablation generator and delivered by an ablation catheter, lesions form in the tissue. Electrodes mounted on or in ablation catheters are used to create tissue necrosis in cardiac tissue to correct conditions such as atrial arrhythmia (including, but not limited to, ectopic atrial tachycardia, atrial fibrillation, and atrial flutter). Arrhythmia (i.e., irregular heart rhythm) can create a variety of dangerous conditions including loss of synchronous atrioventricular contractions and stasis of blood flow which can lead to a variety of ailments and even death. It is believed that the primary cause of atrial arrhythmia is stray electrical signals within the left or right atrium of the heart. The ablation catheter imparts ablative energy (e.g., radiofrequency energy, cryoablation, lasers, chemicals, high-intensity focused ultrasound, etc.) to cardiac tissue to create a lesion in the cardiac tissue. This lesion disrupts undesirable electrical pathways and thereby limits or prevents stray electrical signals that lead to arrhythmias.

One candidate for use in therapy of cardiac arrhythmias is electroporation. Electroporation therapy involves electric-field induced pore formation on the cell membrane. The electric field may be induced by applying a direct current (DC) signal delivered as a relatively short duration pulse which may last, for instance, from a nanosecond to several milliseconds. Such a pulse may be repeated to form a pulse train. When such an electric field is applied to tissue in an in vivo setting, the cells in the tissue are subjected to trans-membrane potential, which essentially opens up the pores on the cell wall, hence the term electroporation. Electroporation may be reversible (i.e., the temporally-opened pores will reseal) or irreversible (i.e., the pores will remain open). For example, in the field of gene therapy, reversible electroporation (i.e., temporarily open pores) are used to transfect high molecular weight therapeutic vectors into the cells. In other therapeutic applications, a suitably configured pulse train alone may be used to cause cell destruction, for instance by causing irreversible electroporation.

Generally, for use in electrophysiological (EP) applications, the success of electroporation therapy cannot be assessed instantaneously, such as in RF ablation. Instead, a clinician may have to wait a week or more after delivering the therapy to clinically detect any therapeutic effects. In the use of electroporation in cancer treatments, where the therapeutic objective is to arrest tumor growth as well as to kill the tumor cell, confirmation of the therapeutic success based on the resolution of the tumor over a prolonged duration is common. However, such delayed therapeutic confirmation poses a severe limitation in using electroporation therapy in EP applications.

As further background for the case of cardiac ablation, physicians customarily use a three-step process: (1) performing diagnostic procedures to identify the heart sites responsible for the arrhythmias; (2) delivering therapy, such as ablation, to the identified sites, based on the results of the diagnostic procedure; and (3) monitoring the progress of the therapy during delivery as well as afterwards to confirm its success (e.g., such as reduction of electrogram and restoration of sinus rhythm). For electroporation to be adopted as a therapeutic step, for instance to be used in step number two above, a procedure to monitor and confirm the progress and ultimate success of the electroporation therapy is needed. In addition, another feature of known electroporation apparatus is that they are characterized by electrode assemblies that produce an omni-directional electric field, which may undesirably affect non-target tissue. It would be desirable to provide an apparatus with greater selectivity with respect to what tissue is to be affected by the therapy.

In addition, it is also known to use radio frequency (RF) energy for ablation purposes in certain therapeutic applications. RF ablation is typically accomplished by transmission of RF energy using an electrode assembly to ablate tissue at a target site. Because RF ablation may generate significant heat, which if not controlled can result in undesired or excessive tissue damage, such as steam pop, tissue charring, and the like, it is common to include a mechanism to irrigate the target area with biocompatible fluids, such as a saline solution. Another known mechanism to control heat is to provide an ablation generator with certain feedback control features, such as a temperature readout of the electrode temperature. To provide for such feedback to the physician/clinician during the procedure, conventional RF ablation generators are typically configured for connection to a temperature sensor, such as a thermocouple or thermistor, that is located within the ablation electrode.

However, the use of either thermocouples or thermistors has spatial limitations in terms of its placement in the electrode. A common conventional irrigated ablation catheter design involves the use of a distal irrigation passageway in combination with an electrode-disposed thermal sensor. The distal irrigation passageway may be thermally insulated and is typically located on the center axis of the electrode assembly. Because the distal irrigation passageway is located on the center axis, the thermal sensor must be moved away from the center axial position. This off-center positioning of the thermal sensor is less than ideal since it could affect the temperature measurement. For example, consider the situation where the catheter electrode is in a parallel contact orientation. The temperature reading will depend on which side of the electrode is contacting the tissue, since it is on the contact side of the electrode where the significant heat will be generated (i.e., with the sensor being either closer to the contact-side for a higher temperature reading or farther away from the contact-side for a lower temperature reading). Moreover, typical thermocouples and/or thermistors are connected to external circuitry by way of wire conductors. Accordingly, these conventional arrangements are susceptible to radio-frequency interference (RFI) and/or electromagnetic interference (EMI) by virtue of at least these connecting wires.

Electroporation therapy generally does not appreciably increase the temperature of the tissue as in RF ablation to give rise to thermally mediated coagulum necrosis. Hence the use of thermal sensors to monitor the creation of tissue necrosis from electroporation is generally redundant. Moreover, duration of electric pulses used to cause tissue necrosis by electroporation is much shorter than the time constants of the thermal sensors generally used in RF ablation applications. Therefore, a new way to monitor the efficacy of creating tissue necrosis due to electroporation is needed.

There is therefore a need for catheter systems that minimize or eliminate one or more of the problems as set forth above.

BRIEF SUMMARY OF THE INVENTION

One advantage of the methods and apparatus described, depicted and claimed herein relates to, in direction-sensitive electrode assembly embodiments for electroporation therapy, an increased selectivity in what tissue is subjected to the electroporation therapy. Another advantage of the methods and apparatus described, depicted and claimed herein relates to, in optical-based tissue sensing embodiments for electroporation therapy, an improved procedure for monitoring both the progress as well as the ultimate success of the therapy. A still further advantage of the methods and apparatus described, depicted and claimed herein relates to, in fiber optic temperature sensing embodiments, an improved accuracy in electrode temperature measurement by avoiding errors that would otherwise arise due to thermal sensor location eccentricity (as described in the Background) as well as providing immunity to RFI and EMI.

In a first aspect, this disclosure is directed to an electroporation therapy system that comprises a device (e.g., a catheter) having proximal and distal ends, an electrode assembly, a detector and an electroporation generator. The electrode assembly includes a plurality of electrically isolated electrode elements disposed at the distal end of the device. The detector is coupled to the plural electrode elements and is configured to identify which elements have a conduction characteristic indicative of contact with tissue that is to be subjected to the electroporation therapy. In an embodiment, the system may further include a tissue sensing circuit configured to determine a tissue property (as sensed through an electrode element or pair thereof) in order to determine whether that element (or pair) is in tissue contact. Once the electrode elements in tissue-contact have been identified, the electroporation generator energizes the identified electrode elements in accordance with an electroporation energization strategy.

In one embodiment, the plurality of electrode elements is arranged in a pic-shaped pattern forming a generally hemispherical-shaped distal surface where the elements are separated from adjacent elements by respective inter-element gaps. When this embodiment is used for either electroporation-induced primary necrosis therapy or electric-field-induced apoptosis (or secondary necrosis) therapy, the energizing strategy carried out by the generator will corresponds to these therapies (i.e., generate the appropriate pulse or pulses). When this embodiment is used for electroporation-mediated therapy, in addition the catheter may be configured with a lumen extending longitudinally through a shaft thereof to the electrode assembly and which is configured to deliver an electrolyte. The electrode assembly includes irrigation ports, which may comprise the inter-element gaps described above (e.g., either open or occupied by a porous material). The electrolyte is delivered to the tissue site and enters the cell through the pores temporarily opened due to electroporation, modifying a property (e.g., a conduction characteristic) of the tissue to improve, for example, a subsequent ablation therapy. Alternatively, an outermost surface of the electrode assembly may comprise chemical-eluting materials, which also enter the cell in the same manner and alter a tissue property for a beneficial effect during a subsequent therapy. The tissue sensing circuit may be further configured to confirm that a predetermined modification of a tissue property has occurred, in accordance with the chosen electroporation therapy.

In another embodiment, the plurality of electrode elements are arranged in at least a first array disposed on an outer surface of a tubular base formed of electrically-insulating material. The array may extend along a first path having a shape substantially matching that of the base. The electroporation generator is configured to selectively energize identified electrode elements of the array in a bipolar fashion so as to produce a lesion (e.g., a narrow, linear lesion when the array has a straight shape). In an alternate embodiment, a second array is provided on the tubular base where the generator selectively energizes elements from both arrays in a bipolar or multi-polar fashion to produce a wider lesion. The shape may be selected from the group comprising a linear shape, an arcuate shape, a L-shape, a question-mark shape or a spiral shape or any other medically useful shape.

In still further embodiments, the plurality of electrode elements are arranged in a plurality of arrays (multi-array) disposed on a base formed of electrically-insulating material. The arrays may be arranged in a fan-shaped pattern or other medically-useful patterns that are configured to produce a distributed or wide area lesion. In all the embodiments of the first aspect of the disclosure, the conductive element detector, preferably using the tissue sensing circuit, identifies those electrode elements that are in contact with tissue wherein the electroporation generator energizes only those elements, thereby improving selectivity in what tissue areas are subjected to the therapy. In addition, the tissue sensing circuit may be used to confirm that a tissue property has be modified in accordance with the chosen electroporation therapy.

In a second aspect, the disclosure is directed to a system for optically monitoring electroporation therapy at a tissue site, and which involves first delivering an electrochromic dye to or at the target tissue site (which delivery may be achieved either in situ or systemically). The monitoring system includes a light source, an optical detector, a catheter carrying first and second optic fibers and a light analyzer. The light source is configured to generate a first light signal. The first optic fiber is transmits the first light signal to its distal end and is directed towards (i.e., is incident upon) the tissue site. The second optic fiber is configured to transmit a second light signal acquired at the tissue site (at its distal end) to the optical detector. The optical detector is configured to detect the second light signal and produce a corresponding output signal. The light analyzer configured to (i) assess the detector output signal at a first time after an electrochromic dye has been delivered to or applied at the tissue site but before an electric field has been applied in order to establish a first, baseline optical characteristic of the second (received) light signal; (ii) monitor the detector output signal at a second time after the electric field has been applied to determine a second optical characteristic that exhibits a color change indicative of an optical radiation storm that accompanies a desired electric field strength; and (iii) monitor the detector output signal at a third time after the second time (e.g., after the electric field has been discontinued) for a third optical characteristic having an intensity that is reduced relative to that of the baseline, which is indicative of an optical black-out representing an effective electroporation therapy. Through the foregoing, the progress of the therapy can be confirmed as well as the ultimate success.

In a third aspect, the disclosure is directed to a temperature sensing catheter system that involves the use of thermochromic or thermotropic materials. The system includes a light source, an optical detector, an electrode catheter and an analyzer. The light source is configured to generate a first light signal. The electrode catheter includes (i) a shaft having proximal and distal ends; (ii) an electrode disposed at the distal end of the shaft where the electrode has a body with an outer surface and a cavity defining an inner surface; and (iii) an optic fiber. At least one of the cavity or the inner surface comprises a thermochromic or thermotropic material configured to change color as a function of temperature. The optic fiber has a distal end that is in optical communication with the cavity and a proximal end. The optic fiber transmits the first light signal (from the light source) to its distal end where it is projected towards the cavity. The optic fiber is further configured to carry a second light signal acquired at its distal end back to its proximal end. The optical detector is configured to detect the second light signal and produce a corresponding output signal. The analyzer is configured to assess the detector output signal and generate a temperature signal indicative of the electrode temperature. In an embodiment, the analyzer may use predetermined calibration data that correlates a received light spectrum to a temperature.

In further embodiments, at least a portion of the inner surface of the cavity comprises a layer of the thermally-sensitive material (i.e., the thermochromic or thermotropic material) or at least a portion of the inner surface of the cavity is impregnated with the thermally-sensitive material. In another embodiment, a distal lumen of the optic fiber is filled with the thermally-sensitive material such that the optic fiber optic distal end is in optical communication with the thermally sensitive material.

These and other benefits, features, and capabilities are provided according to the structures, systems, and methods depicted, described and claimed herein.

BRIEF DESCRIPTION OF THE DRAWINGS

FIGS. 8-10 are isometric and plan views of a direction-sensitive multi-polar electrode assembly for creating linear lesions using bi-poles from spaced, parallel electrode element lines.

FIGS. 20-21 are partial cross-sectional views of fiber optic temperature sensing system embodiments.

DETAILED DESCRIPTION OF THE INVENTION

Figure 1:
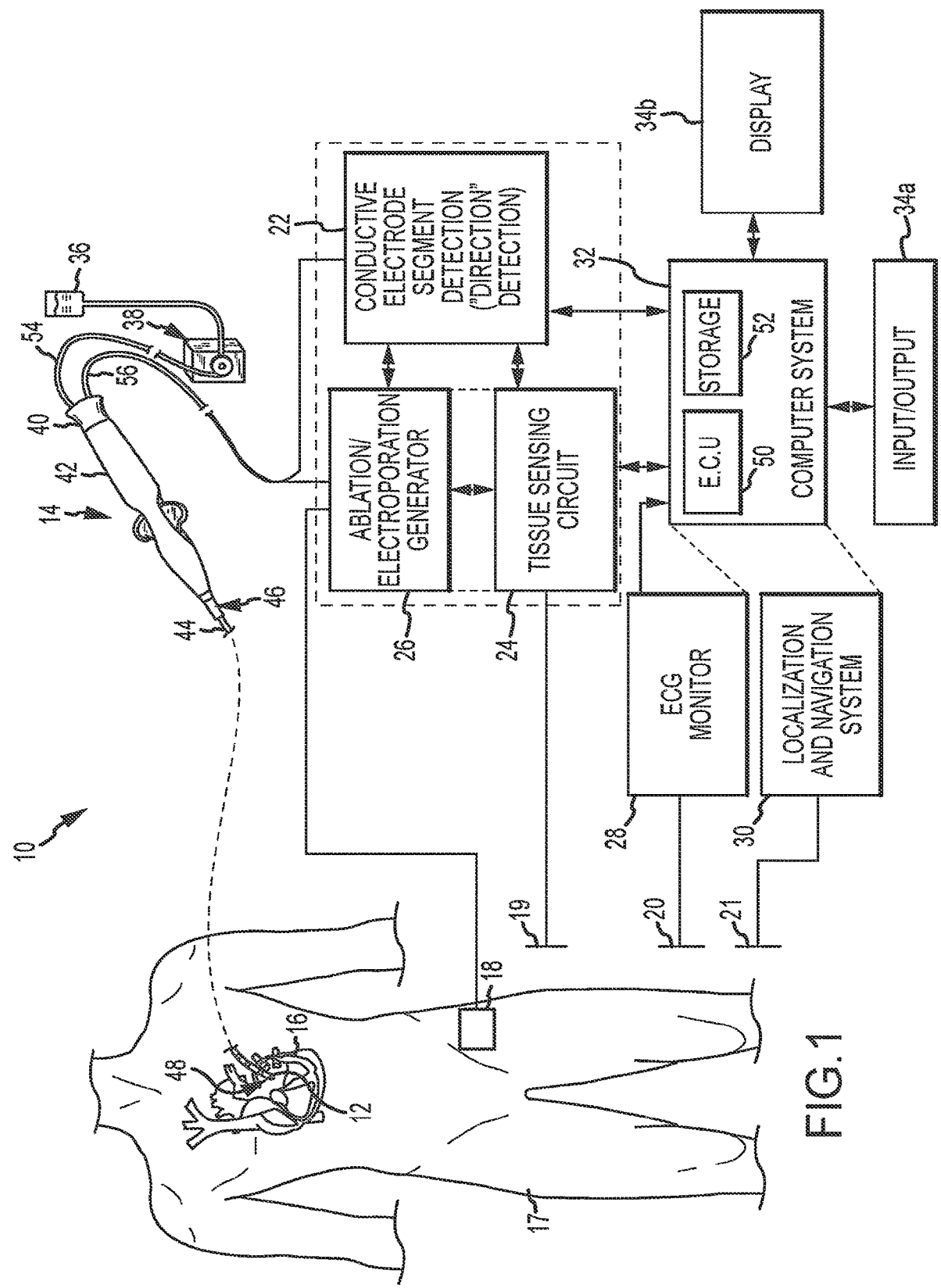
FIG. 1 is a schematic and block diagram view of a system incorporating embodiments for electroporation therapy involving direction-sensitive multi-polar or multi-array catheter electrode assemblies.

Referring now to the drawings wherein like reference numerals are used to identify identical components in the various views, FIG. 1 is a diagrammatic and block diagram view of a system 10 in connection with which direction-sensitive multi-polar or multi-array electrode assemblies for electroporation therapy may be used. In general, the various embodiments include an electrode assembly disposed at the distal end of a catheter. The electrode assembly comprises a plurality of individual, electrically-isolated electrode elements. Each electrode element is individually wired such that it can be selectively paired or combined with any other electrode element to act as a bipolar or a multi-polar electrode for both sensing (more below) and electroporation energization purposes. FIGS. 2-17 show various embodiments featuring direction-sensitive multi-polar or multi-array electrode assemblies. In the sensing mode, the electrode elements are electrically scanned to detect or identify which electrode elements (or pairs) have electrical conduction characteristics indicative of contact with the target tissue (e.g., impedance, phase angle, reactance). Once such electrode elements have been identified, an electroporation generator is controlled to energize the identified electrode elements in accordance with an electroporation energization strategy. The selective energization improves selectivity of the target tissue, more effectively directing the therapy to just the desired, target tissue. The particular energization strategy chosen will depend on the particular type of electroporation therapy sought to be achieved. Exemplary electroporation therapies include: (1) electroporation-mediated therapy; (2) electroporation-induced primary necrosis therapy; and (3) electric field-induced apoptosis (or secondary necrosis) therapy. Each therapy will be described below.

Electroporation-mediated ablation therapy refers to delivering tissue pre-conditioning effects using electroporation. Pre-conditioning effects would lead to altering the biophysical properties of the tissue which would make the tissue receptive to other ablative therapies such as radio-frequency (RF), ultrasound, and photodynamic therapy. Tissue pre-conditioning may be achieved by delivering electrolytes to the tissue locally using electroporation, thereby changing the biophysical properties of the tissue such as its electrical, acoustical, optical, thermal, and perfusion properties. In this case, the electric field applied to the tissue causes transient and reversible effects of temporarily opening the pores on the cell wall, and the cell remains viable after the application of the electric field. In general, electroporation will involve the application of direct current (DC) or very low frequency alternating current (AC) to create an electric field sufficient to "tear" the lipid bilayer that forms the cell membrane. There are many voltage level/pulse duration/duty cycle combinations that may be effective (e.g., in one instance involving embryonic chick hearts, the tissue was placed between electrodes spaced 0.4 cm apart and subjected to a series of 200 V/cm electrical stimuli from a commercial stimulator where varying numbers of 10 millisecond pulses were applied 10 seconds apart). It should be understood that a plurality of factors may affect the particular energization scheme needed to achieve the temporary (i.e., transient and reversible) opening of pores on the cell wall, including species, tissue size, cell size and development stage.

Electroporation-induced primary necrosis therapy refers to the effects of delivering electrical current in such manner as to directly cause an irreversible loss of plasma membrane (cell wall) integrity leading to its breakdown and cell necrosis. This mechanism of cell death may be viewed as an "outside-in" process, meaning that the disruption of the outside wall of the cell causes detrimental effects to the inside of the cell. Typically, for classical plasma membrane electroporation, electric current is delivered as a pulsed electric field in the form of short-duration direct current (DC) pulses (e.g., 0.1 to 20 ms duration) between closely spaced electrodes capable of delivering a relatively low electric field strength of about 0.1 to 1.0 kV/cm.

Electric-field-induced apoptosis (or secondary necrosis) therapy refers to the effects of delivering electrical current in such a manner as to cause electromanipulation of the intracellular structures (e.g., such as the nucleus, mitochondria or endoplasmic reticulum) and intracellular functions that precede the disassembly of the cell and irreversible loss of plasma membrane (cell wall). This mechanism of cell death may be viewed as an "inside-out" process, meaning that the disruption of the inside of the cell causes detrimental "secondary" effects to the outside wall of the cell. For electric field-induced apoptosis, electric current is delivered as a pulsed electric field in the form of extremely short-duration DC pulses (e.g., 1 to 300 ns duration) between closely spaced electrodes capable of delivering a relatively high electric field strength of about 2 to 300 kV/cm.

It should be understood that while the energization strategies for electroporation-mediated ablation therapy, electroporation-induced primary necrosis therapy, electric-field-induced apoptosis (or secondary necrosis) therapy are described as involving DC pulses, embodiments may use variations and remain within the spirit and scope of the invention. For example, exponentially-decaying pulses, exponentially-increasing pulses, mono-phase or bi-phase pulses and combinations of one or more all may be used.

Accordingly, the electroporation embodiments described and depicted herein involve two different modes of therapy: (1) usage of electroporation therapy to destroy tissue (i.e., cell death) and (2) electroporation-mediated therapy where electroporation mechanism is used to modify a tissue property (e.g., conductivity, reactance, responsiveness/irresponsiveness to photonic energy, responsiveness/irresponsiveness to ultrasonic energy, etc.) for subsequent tissue sensing and/or ablation (e.g., via electrical tissue sensing or electrical energy delivery such as RF energy deliver, via photodynamic-based sensing and/or energy delivery, via ultrasound-based sensing and/or energy delivery, etc.).

As to the first mode of therapy mentioned above (i.e., electroporation alone), it should be understood that electroporation is not substantially energy-dissipative and thus does not substantially thermally alter the target tissue (i.e., does not substantially raise its temperature), thereby avoiding possible thermal effects (e.g., possible pulmonary vein stenosis when using RF energy for a pulmonary vein isolation (PVI) procedure). Even to the extent that RF energy based ablation is used only as a "touch up" after an initial round of electroporation therapy, the thermal effects are reduced due to the corresponding reduction in the application of RF energy. This "cold therapy" thus has desirable characteristics.

As to the second mode mentioned above (i.e., electroporation-mediated therapy), electrochromic dyes may be used for effective monitoring of the progress of and completion of electroporation therapy to condition the target tissue. In the first mode, however, the use of electrochromic dyes do not come into play.

With this background, and now referring again to FIG. 1, the system 10 includes a direction-sensitive multi-polar or multi-array catheter electrode assembly 12 configured to be used as briefly outlined above and as described in greater detail below. The electrode assembly 12 is incorporated as part of a medical device such as a catheter 14 for electroporation therapy of tissue 16 in a body 17 of a patient. In the illustrative embodiment, the tissue 16 comprises heart or cardiac tissue. It should be understood, however, that embodiments may be used to conduct electroporation therapy with respect to a variety of other body tissues.

FIG. 1 further shows a plurality of patch electrodes designated 18, 19, 20 and 21, which are diagrammatic of the body connections that may be used by the various sub-systems included in the overall system 10, such as a detector 22, a tissue sensing circuit 24, an energization generator 26 (e.g., electroporation and/or ablation depending on the embodiment), an EP monitor such as an ECG monitor 28 and a localization and navigation system 30 for visualization, mapping and navigation of internal body structures. It should be understood that the illustration of a single patch electrode is diagrammatic only (for clarity) and that such sub-systems to which these patch electrodes are connected may, and typically will, include more than one patch (body surface) electrode. The system 10 may further include a main computer system 32 (including an electronic control unit 50 and data storage—memory 52), which may be integrated with the system 30 in certain embodiments. The system 32 may further include conventional interface components, such as various user input/output mechanisms 34a and a display 34b, among other components.

The detector 22 is coupled to the plurality of electrode elements of the electrode assembly 12 and in one embodiment is configured to identify which elements have characteristics (e.g., if electrical characteristics, then for example, impedance, phase angle, reactance, etc.) indicative of contact of the electrode element with tissue 16. In embodiments where the electrode elements cover up to 360 degrees (e.g., a distal tip in hemispherical shape), it is desirable to energize only those electrode elements that are in contact with tissue, as described above. This may be thought of as a "direction-sensitive" since determining what electrode elements are in contact with tissue also determines the "direction" of the therapy to be delivered to the tissue.

A tissue sensing circuit 24 may be used in connection with the detector 22 for determining an characteristic (e.g., electrical characteristic) to be used in making a "contact" versus "no contact" decision for each electrode element (or pair thereof). In an embodiment, the detector 22 may be configured to scan (probe) the electrode elements (or pairs) and record the identification of such in-contact electrode elements. The detector 22, the tissue sensing circuit 24 and the generator 26 are enclosed in a dashed-line box in FIG. 1 to indicate the contemplated cooperation necessary to perform the functions described herein. However, it should be understood that no necessary physical integration is implied (i.e., these blocks may be embodied as physically separate components). More particularly, any one of the detector 22, the tissue sensing circuit or the generator 26 may be implemented as a stand-alone component or may be implemented in another portion of system 10 provided such other portion has adequate capabilities to perform the desired function(s).

The tissue sensing circuit 24 as noted above is configured to determine an electrical characteristic associated with an electrode element or pair for purposes of determining whether the electrode element (or pair) is in contact with the tissue 16. The characteristic, when electrical in nature, may be an impedance, a phase angle, a reactance or an electrical coupling index (ECI), as seen by reference to co-pending U.S. patent application Ser. No. 12/622,488, filed Nov. 20, 2009 entitled "SYSTEM AND METHOD FOR ASSESSING LESIONS IN TISSUE", owned by the common assignee of the present invention and hereby incorporated by reference in its entirety. In such an embodiment, multiple skin patch electrodes may be used. Skin (body surface) patch electrodes may be made from flexible, electrically conductive material and are configured for affixation to the body 17 such that the electrodes are in electrical contact with the patient's skin. In one embodiment, the circuit 24 may comprise means, such as a tissue sensing signal source (not shown), for generating an excitation signal used in impedance measurements (e.g., the excitation signal being driven through the subject electrode element) and means, such as a complex impedance sensor (not shown), for determining a complex impedance or for resolving the detected impedance into its component parts. Other patch electrodes (shown only diagrammatically as electrode 19) may preferably be spaced relatively far apart and function as returns for an excitation signal generated by the tissue sensing circuit 24 (as described in U.S. application Ser. No. 12/622,488). As to spacing, tissue sensing patch electrodes (shown only diagrammatically as electrode 19) may be two in number located respectively on the medial aspect of the left leg and the dorsal aspect of the neck or may alternatively be located on the front and back of the torso or in other conventional orientations. Of course, other implementations are possible.

The detector 22 may receive the measured characteristic from tissue sensing circuit 24 and then determine whether the subject electrode element is in tissue contact based on the value of the determined electrical characteristic, along with predetermined threshold data and decision rules (e.g., if computer-implemented, programmed rules). As shown, the tissue sensing circuit 24 may be coupled through the generator 26 and may use the same conductors to the electrode assembly 12 for excitation purposes as used by the generator 26 for energization purposes.

The electroporation generator 26 is configured to energize the identified electrode elements in accordance with an electroporation energization strategy, which may be predetermined or may be user-selectable. The generator 26 may be configured to communicate with the detector 22 to receive a signal or data set indicative of the electrode elements previously identified during the scanning phase as being in tissue contact. The electroporation energizing strategies (e.g., bi-poles, multi-poles, pulse magnitude, number and duration, etc.) are defined based on their correspondence to a respective one of the electroporation therapies described above, namely: (1) electroporation-mediated therapy; (2) electroporation-induced primary necrosis therapy; and (3) electric field-induced apoptosis (or secondary necrosis) therapy.

For electroporation-mediated therapy, the generator 26 may be configured to produce an electric current that is delivered via the electrode assembly 12 as a pulsed electric field in the form described above.

For electroporation-induced primary necrosis therapy, the generator 26 may be configured to produce an electric current that is delivered via the electrode assembly 12 as a pulsed electric field in the form of short-duration direct current (DC) pulses (e.g., 0.1 to 20 ms duration) between closely spaced electrodes capable of delivering a relatively low electric field strength (i.e., at the tissue site) of about 0.1 to 1.0 kV/cm.

For electric field-induced apoptosis therapy, the generator 26 may be configured to produce an electric current that is delivered via the electrode assembly 12 as a pulsed electric field in the form of extremely short-duration direct current (DC) pulses (e.g., 1 to 300 ns duration) between closely spaced electrodes capable of delivering a relatively high electric field strength (i.e., at the tissue site) of about 2 to 300 kV/cm.

In certain other embodiments (e.g., electroporation-mediated ablation therapy), both electroporation specific energy as well as ablation specific energy will be used in the overall process and in such embodiments, the generator 26 may be further configured to deliver ablation energy as well, or another device may be provided to supply the ablation energy.

For example, in the case of electroporation-mediated ablation therapy (i.e., electroporation to modify tissue characteristics then followed by RF ablation), the generator 26 may be further configured to generate, deliver and control RF energy output by the electrode assembly 12 of the catheter 14. An ablation energizing power source portion of generator 26 may comprise conventional apparatus and approaches known in the art, such as may be found in commercially available units sold under the model number IBI-1500T RF Cardiac Ablation Generator, available from Irvine Biomedical, Inc. In this regard, the ablation functional portion of the generator 26 may be configured to generate a signal at a predetermined frequency in accordance with one or more user specified parameters (e.g., power, time, etc.) and under the control of various feedback sensing and control circuitry as is known in the art. For example, the RF ablation frequency may be about 450 kHz or greater, in certain embodiments. Various parameters associated with the ablation procedure may be monitored including impedance, the temperature at the tip of the catheter, ablation energy and the position of the catheter and provide feedback to the clinician regarding these parameters. As to ablation therapy, the electrode 18 may function as an RF indifferent/dispersive return for an RF ablation signal (in certain embodiments).

With continued reference to FIG. 1, as noted above, the catheter 14 may comprise functionality for electroporation and in certain embodiments (i.e., electroporation-mediated ablation therapy) also an ablation function (e.g., RF ablation). It should be understood, however, that in those embodiments, variations are possible as to the type of ablation energy provided (e.g., cryoablation, ultrasound, etc.). For example, the embodiment shown in FIG. 1 includes a fluid source 36 having a biocompatible fluid such as saline or other electrolyte suitable for the electroporation-mediated therapy chosen, which may be delivered through a pump 38 (which may comprise, for example, a fixed rate roller pump or variable volume syringe pump with a gravity feed supply from the fluid source 36 as shown) for delivery of a suitable electrolyte for electroporation-mediated ablation or saline for irrigation.

In the illustrative embodiment, the catheter 14 includes a cable connector or interface 40, a handle 42, a shaft 44 having a proximal end 46 and a distal 48 end. As used herein, "proximal" refers to a direction toward the end of the catheter near the clinician and "distal" refers to a direction away from the clinician and (generally) inside the body of a patient. The catheter 14 may also include other conventional components not illustrated herein such as a temperature sensor, additional electrodes, and corresponding conductors or leads. The connector 40 provides mechanical, fluid and electrical connection(s) for cables 54, 56 extending from the pump 38 and the generator 24. The connector 40 may comprise conventional components known in the art and as shown may is disposed at the proximal end of the catheter 14.

The handle 42 provides a location for the clinician to hold the catheter 14 and may further provide means for steering or the guiding shaft 44 within the body 17. For example, the handle 42 may include means to change the length of a guidewire extending through the catheter 14 to the distal end 48 of the shaft 44 or means to steer the shaft 44. The handle 42 is also conventional in the art and it will be understood that the construction of the handle 42 may vary. In an alternate exemplary embodiment, the catheter 14 may be robotically driven or controlled. Accordingly, rather than a clinician manipulating a handle to advance/retract and/or steer or guide the catheter 14 (and the shaft 44 thereof in particular), a robot is used to manipulate the catheter 14.

The shaft 44 is an elongated, tubular, flexible member configured for movement within the body 17. The shaft 44 is configured to support the electrode assembly 12 as well as contain associated conductors, and possibly additional electronics used for signal processing or conditioning. The shaft 44 may also permit transport, delivery and/or removal of fluids (including irrigation fluids and bodily fluids), medicines, and/or surgical tools or instruments. The shaft 44 may be made from conventional materials such as polyurethane and defines one or more lumens configured to house and/or transport electrical conductors, fluids or surgical tools. The shaft 44 may be introduced into a blood vessel or other structure within the body 17 through a conventional introducer. The shaft 44 may then be advanced/retracted and/or steered or guided through the body 17 to a desired location such as the site of the tissue 16, including through the use of guidewires or other means known in the art.

The localization and navigation system 30 may be provided for visualization, mapping and navigation of internal body structures. The system 30 may comprise conventional apparatus known generally in the art (e.g., an EnSite NAVX™ Navigation and Visualization System, commercially available from St. Jude Medical, Inc. and as generally shown with reference to commonly assigned U.S. Pat. No. 7,263,397 titled "Method and Apparatus for Catheter Navigation and Location and Mapping in the Heart," the entire disclosure of which is incorporated herein by reference). It should be understood, however, that this system is exemplary only and not limiting in nature. Other technologies for locating/navigating a catheter in space (and for visualization) are known, including for example, the CARTO navigation and location system of Biosense Webster, Inc., the AURORA® system of Northern Digital Inc., commonly available fluoroscopy systems, or a magnetic location system such as the gMPS system from Mediguide Ltd. In this regard, some of the localization, navigation and/or visualization system would involve a sensor be provided for producing signals indicative of catheter location information, and may include, for example one or more electrodes in the case of an impedance-based localization system, or alternatively, one or more coils (i.e., wire windings) configured to detect one or more characteristics of a magnetic field, for example in the case of a magnetic-field based localization system.

Figure 2:
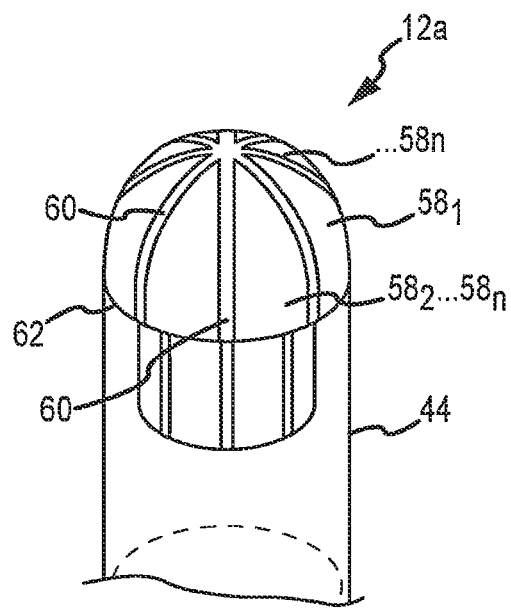
FIGS. 2-4 are isometric and plan views of a direction-sensitive multi-polar tip electrode assembly.
Figure 3:
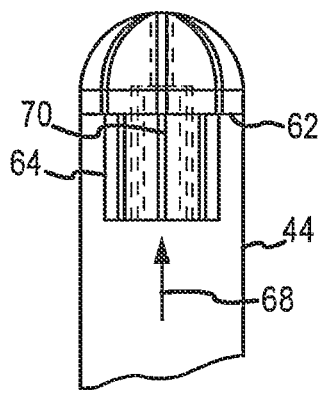
Figure 4:
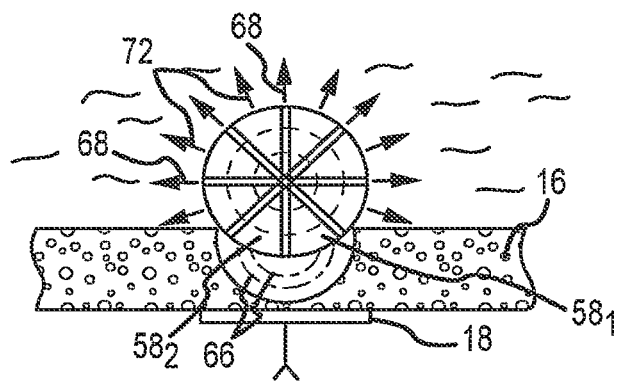

FIGS. 2-4 are isometric and plan views of a direction-sensitive multi-polar electrode assembly, in one embodiment designated electrode assembly 12a. The electrode assembly 12a includes a plurality of electrically-conductive electrode elements $58_1, 58_2, \ldots, 58_n$ that are separated from adjacent elements by respective inter-element gaps, shown at 60. The electrode elements $58_1, 58_2, \ldots, 58_n$ may be left open (i.e., unobstructed) or filled with porous material, for example, for irrigation purposes, or may alternatively be sealed with electrically-insulative filler material. In the illustrative embodiment, the electrode elements $58_1, 58_2, \ldots, 58_n$ are arranged in a pie-shaped pattern where all the individual electrode elements are approximately the same size and shape. In one embodiment, the distal surface of electrode assembly 12a may be rounded (e.g., partially spherical or hemispherical), although other configurations may be used. The individual elements $58_1, 58_2, \ldots, 58_n$ are further arranged so that collectively they form a proximally-facing shoulder portion 62. In addition, the electrode assembly 12a has a proximally-extending stub 64 (best shown in FIG. 3) having a first diameter that reduced relative to the a second diameter of the outermost surface of the pie-shaped pattern of electrode elements $58_1, 58_2, \ldots, 58_n$.

The electrode elements $58_1, 58_2, \ldots, 58_n$ may comprise conventionally employed electrically-conductive materials, such as, generally, metals or metal alloys. Examples of suitable electrically conductive materials include (but are not limited to) gold, platinum, iridium, palladium, stainless steel, and various mixtures, alloys and combinations thereof. In alterative embodiments, the electrode elements $58_1, 58_2, \ldots, 58_n$ may comprise a so-called conforming (brush) electrode configuration, as seen by reference to U.S. Pat. No. 7,326,204 to Paul et al. entitled "BRUSH ELECTRODE AND METHOD FOR ABLATION", owned by the common assignee of the present invention and the entire disclosure of which is hereby incorporated by reference herein. Paul et al. disclose, generally, an electrically conductive electrode formed from a plurality of flexible filaments or bristles for applying ablative energy (e.g., RF energy) and facilitates electrode-tissue contact in target tissue having flat or contoured surfaces. Other electrode configurations known in the art may also be used in the electroporation systems described herein.

FIG. 4 is a partial, cross-sectional view of the electrode assembly 12a in contact with tissue 16. In a first embodiment, the system 10, including the electrode assembly 12a, may be used for a method involving either electroporation-induced primary necrosis therapy or electric field-induced apoptosis therapy (or secondary necrosis therapy).

The method begins with a clinician, such as a physician, maneuvering the catheter 14, including the electrode assembly 12a, to the desired site where tissue 16 is located. In this regard, previous mapping exercises may have been conducted which has resulted in a map of the patient's anatomy that will be the subject of the electroporation therapy. Such a map may be used in navigating the catheter 14 to the site.

Once at the site, the physician controls the catheter 14 such that the distal end of the electrode assembly 12a is against the tissue 16.

The next step involves identifying which electrode elements $58_1, 58_2, \ldots, 58_n$ are in contact with the tissue, using the detector 22 and the tissue sensing circuit 24, as described above. The detector 22 may record the identification of the electrode elements $58_1, 58_2, \ldots, 58_n$ (or pairs thereof) for subsequent use in controlling energization during the electroporation therapy. In the illustrative example in FIG. 4, the electrode elements identified as being in contact with the tissue 16 include electrode elements $58_1$ and $58_2$.

The next step involves energizing the identified electrode elements (i.e., those elements that are in contact with tissue—namely, electrode elements $58_1$ and $58_2$ in the example of FIG. 4) using the electroporation generator 26 in accordance with an energization strategy. The energization strategy used in turn will be based on the chosen electroporation therapy. In this first embodiment, the therapies include either electroporation-induced primary necrosis therapy or electric field-induced apoptosis therapy (or secondary necrosis therapy). Accordingly, the generator 26 is controlled to deliver electrical energy consistent with the electrical parameters described above to perform each of these therapies. The energization strategy is preferably conducted in a bipolar fashion (i.e., electrode element to electrode element), which creates local electric fields, designated fields 66. The established, local electric fields cause the desired effect on the tissue cells in accordance with the chosen electroporation therapy.

The next step involves determining whether the sought-after modification to a property of the target tissue 16 has occurred. Preferably, this step is also performed using tissue sensing circuit 24. Depending on the property sought to be modified, achieving the desired property modification can be confirmed by a physician monitoring a readout or the like of the measured or computed tissue property of interest (e.g., a read-out from the tissue sensing circuit 24 or display that is in communication with the tissue sensing circuit). In an alternate embodiment, the tissue sensing circuit 24 (or other component via suitable communication) may be configured to generate a signal indicative of when the desired tissue modification has been achieved (e.g., a pre-set threshold). Once the desired modification to the tissue property has been achieved, the electroporation therapy to the target tissue 16 can be discontinued (i.e., the applied electric field discontinued).

In one embodiment, the system is configured such that a tissue property is monitored substantially continuously during therapy (i.e., the tissue sensing circuit 24 is configured to monitor the tissue property of interest concurrently with electric field generation). In this embodiment, the physician is able to use real time feedback to determine when to discontinue the therapy. In an alternate embodiment, the system may be configured to blank the tissue sensing circuit 24 output during high voltage switching of the electroporation generator. The foregoing assumes that the sensing circuit 24 is based on electrical measurements taken from electrodes. In a still further embodiment, the sensing circuit may be light based and thus immune from high voltage interferences produced by virtue of the electroporation generator, since any light-to-voltage converters will be located outside the body, thereby isolating the downstream electronics from the interference. In a still further embodiment, the method is sequential, where the physician switches between applying power (therapy) and tissue sensing (property measurement) and continues iterating until completion (e.g., energize-check tissue property, energize-check tissue property, energize-check tissue property, etc.). In yet another embodiment, the physician will check the tissue property (using tissue sensing circuit 24) after completing a predefined instance of therapy (e.g., X minutes of therapy at predetermined conditions).

With continued reference to FIGS. 2-4, the electrode assembly 12a may be used in an alternate way for performing electroporation-mediated ablation therapy. In this regard, the electrode assembly 12a is used to effect transient and reversible electroporation, along with the delivery of a suitable chemical adapted to improve subsequent therapy such as RF ablation. Accordingly, in this alternate embodiment, the electrode assembly 12a, with the exception of the changes to be described below, may the same as described above. The electrode assembly 12a may be configured to deliver a chemical, which may be for example an electrolyte 68 (FIGS. 3 and 4) in proximity to the tissue 16.

In the case of delivery of a liquid chemical (electrolyte), the shaft 44 may include at least one lumen (omitted for clarity) extending longitudinally therethrough to carry the electrolyte 68 from a source 36 (FIG. 1) to the electrode assembly 12a. The electrode assembly 12a includes a channel 70 intermediate the lumen (not shown) and one or more irrigation ports on the distal surface of the electrode assembly 12a. The channel 70 may comprise either the inter-element gaps 60 (free of any material), the inter-elements gaps 60 (filled with a porous material) or one ore more dedicated passages (not shown) through one or more of the electrode elements $58_1, 58_2, \ldots, 58_n$ which terminate in discrete irrigation ports on the distal surface.

In an alternate embodiment, the chemical is delivered locally. For example, the outermost, distal surface of the electrode assembly 12a may comprise a chemical-eluting material, shown by arrows 72 in FIG. 4 (eluting from the distal surface of the electrode assembly 12). More particularly, at least one of either the outermost surface of the electrode elements $58_1, 58_2, \ldots, 58_n$ or the outermost surface of a material used to fill in the inter-element gap 60 may be modified to exhibit chemical-eluting properties. The chemicals involved in the embodiment comprise those adapted to modify a property of the target tissue 16. As an example, the property may be an electrical conductivity property of the target tissue, such as the fat pads of the ganglionated plexi, which modification renders the target tissue more receptive and amenable to conduction of RF current as used in RF ablation.

With reference to FIG. 4, a method of electroporation-mediated ablation therapy will now be set forth. An initial step of the method involves configuring the electrode assembly 12a with a chemical efflux/eluting capability, as described above. The next step involves maneuvering the catheter, in particular the electrode assembly 12a thereof, to the target tissue site 16, again as described above. Next, identifying which electrode elements $58_1, 58_2, \ldots, 58_n$ are in contact with the tissue 16, again as already described above, using the detector 22 and the tissue sensing circuit 24.

The next step involves energizing the identified electrode elements (i.e., those elements that are in contact with tissue—namely, electrode elements $58_1$ and $58_2$ in the example of FIG. 4) using the electroporation generator 26 in accordance with a suitable energization strategy. The energization strategy used by the generator 26 in this embodiment will be based on electroporation-mediated ablation therapy described above. Accordingly, the generator 26 is controlled to deliver electrical energy consistent with the electrical parameters described above to cause transient and reversible electroporation. The energization strategy is preferably conducted in a bipolar fashion (i.e., electrode element to electrode element), which creates local electric fields that are shown and designated as fields 66. The electric field across the cell membrane is operative to open pores in the cell wall. Simultaneous with the energization step, one or both of (1) the electrolyte 68 or (2) the predetermined chemical 72 are present in the vicinity of the target tissue. With the cell pores opening up due to the electric field 66, either or both of the electrolyte 68 or the chemical 72 are taken into (enter into) the cells of the target tissue to effect the desired modification to at least one property of the target tissue. Again, in one example, the modification for purposes of a subsequent RF ablation therapy involves modifying the electrical conduction properties, of the target tissue 16 to be more receptive and amenable to carrying RF current.

The next step involves determining whether the sought-after modification to a property of the target tissue 16 has been effected. Preferably, this step is also performed using tissue sensing circuit 24. Depending on the property sought to be modified, achieving the desired property modification can be confirmed by a physician monitoring a readout or the like of the measured or computed tissue property of interest (e.g., a read-out from the tissue sensing circuit 24 or a display in communication therewith). In an alternate embodiment, the tissue sensing circuit 24 (or other component via suitable communication) may be configured to generate a signal indicative of when the desired tissue modification has been achieved (e.g., a preset threshold). Once the desired modification to the tissue property has been achieved, the electroporation therapy to the target tissue 16 can be discontinued.

Finally, after the target tissue 16 has been modified, RF ablation is performed on the target tissue 16. In this regard, the generator 26 may include an RF ablation function or a separate RF ablation generator/controller may be used. In either case, in one embodiment, the same electrode elements 58$_i$ that were identified and energized for electroporation therapy are now energized for RF ablation. RF ablation may conducted by energizing the identified electrode elements 58$_i$ in a bipolar fashion (i.e., RF energy being passed between identified electrode elements 58$_i$, or pairs thereof), a multi-polar fashion or a unipolar fashion (i.e., between one or more of the identified electrode elements 58$_i$ and a remote dispersive/indifferent skin patch electrode such as electrode 18, and/or a dispersive electrode on a catheter inside the body, as seen by reference to PCT International Patent Application PCT/US2006/061710 (see FIG. 21 and paragraph [00148]) and corresponding U.S. Patent Publication 2008/0275465, application Ser. No. 12/096,069 entitled "DESIGN OF HANDLE SET FOR ABLATION CATHETER WITH INDICATORS OF CATHETER AND TISSUE PARAMETERS", both owned by the common assignee of the present invention and the entire disclosures of both hereby incorporated by reference herein). Use of such a catheter electrode inside the body may exhibit increased rejection of noise as compared to a body surface electrode. It should be appreciated that the art is replete with configurations and strategies for ablation generally, and RF ablation in particular. Accordingly, the foregoing description is exemplary only and not limiting in nature.

FIGS. 5A-5D and FIGS. 6-7 show a direction-sensitive multi-polar electrode assembly designated 12$b$ suitable for creating linear lesions using bi-poles in the same electrode element line. Unless otherwise described below, the electrical connections and interactions with the components of system 10 will be the same for assembly 12$b$ as was set forth above for assembly 12$a$ and will accordingly not be repeated.

The electrode assembly 12$b$ is configured to be disposed at the distal end 48 of catheter 14. The electrode assembly 12$b$ comprises a plurality of electrode elements (poles) 74$_1$, 74$_2$, . . . 74$_n$ arranged in a first array 76. The electrode elements 74$_1$, 74$_2$, . . . 74$_n$ of the array 76 are distributed contiguously in a linear or arcuate fashion on an outermost surface of a base 78, which in the illustrative embodiment is configured as a tubular structure (sec FIGS. 5A, 6-7). The tubular base 78 comprises electrically-nonconductive material. The individual poles 74$_1$, 74$_2$, . . . 74$_n$ are separated from each other by intervening gaps, which may be impervious or may contain ports or pores (not shown) for irrigation purposes.

The poles 74$_1$, 74$_2$, . . . 74$_n$ of array 76 extend along a first path 80 having a shape substantially matching that of the base 78. In the illustrative embodiment, the tubular base 78 has an axis 82 that is straight such that the first path 80 is also straight and substantially parallel to axis 82. However, the tubular base 78 may, in alternate embodiments (i) be formed in material composition and structure so as to be flexible enough to allow bending into a non-straight shapes; (ii) include mechanisms to impart a shape, such as for example pull wires or the like; or (iii) have a preformed shape. Moreover, the tubular base 78 of the electrode assembly 12$b$ may be shaped relative to the catheter shaft 44 (best shown in FIG. 2) as a substantially straight tube or alternatively, the tubular base 78 may have an arcuate shape such that the shaft/tubular base together take the shape of a hockey stick, a question mark or a spiral. In such other embodiments, the poles 74$_1$, 74$_2$, . . . 74$_n$ may be distributed on the first path 80 such that its shape matches the shape of the arcuate or alternative shaped tubular base 78.

Electrode assembly 12$b$ may include a further plurality of electrode elements defining a second array 84. In the illustrative embodiment, the plurality of electrode elements (poles) of the second array 84 are arranged in a substantially linear fashion, parallel to the axis 82 and parallel to the path 80 along which the poles of the first array 76 extend. In further embodiments, further arrays of electrode elements (poles) may be provided on the outer surface of the tubular base 78, preferably extending along a respective path that is parallel to the axis 82 and also parallel to the other pole paths. Generally, the electrode elements (poles) 74$_1$, 74$_2$, . . . 74$_n$ of the electrode assembly 12$b$ may be formed so as to be substantially flush with the outer surface of the tubular base 78.

In a still further variation of the electrode assembly 12$b$, the tubular base 78 has an arcuate shape, designated base 78$a$. As shown in FIGS. 5B-5C, the arcuate tubular base 78$a$ has electrode elements (poles) 74$_1$, 74$_2$, . . . 74$_n$ placed on the surface (plane) of the arc that is parallel to the longitudinal axis 82$a$ of the catheter shaft (and plane 83 cutting through the electrodes is normal to axis 82$a$), such as like a so-called Lineage PV to create pulmonary vein isolation lines within the pulmonary vein, as seen by reference to U.S. Patent Publication U.S. 2006/0111708, application Ser. No. 11/328, 565 filed Jan. 10, 2006 entitled ABLATION CATHETER ASSEMBLY HAVING A VIRTUAL ELECTRODE COMPRISING PORTHOLES, owned by the common assignee of the present invention and hereby incorporated by reference in its entirety. Alternatively, as shown in FIG. 5D, the arcuate tubular base 78$a$ has electrode elements (poles) 74$_1$, 74$_2$, . . . 74$_n$ placed on the face (plane) of the arc that is normal to the longitudinal axis 82$a$ of the catheter shaft, such as a branding iron configuration, for creating a lesion on the antrum of the pulmonary vein, as seen by reference to U.S. Patent Publication U.S. 2008/0161790, application Ser. No. 11/617,524 filed Dec. 28, 2006 entitled VIRTUAL ELECTRODE ABLATION CATHETER WITH ELECTRODE TIP AND VARIABLE RADIUS CAPABILITY, owned by the common assignee of the present invention and hereby incorporated by reference in its entirety.

FIGS. 8-10 show an alternate construction of a direction-sensitive multi-polar electrode assembly designated 12c suitable for creating linear lesions. Again, unless otherwise described below, the electrical connections and interactions with the components of the system 10 will be the same for assembly 12c as set forth above for assemblies 12a, 12b and will accordingly not be repeated. The electrode elements (poles) $74_1$, $74_2$, ... $74_n$ of the electrode assembly 12c may be formed so as to be slightly raised relative to the outer surface of the tubular base 78.

Figure 5A:
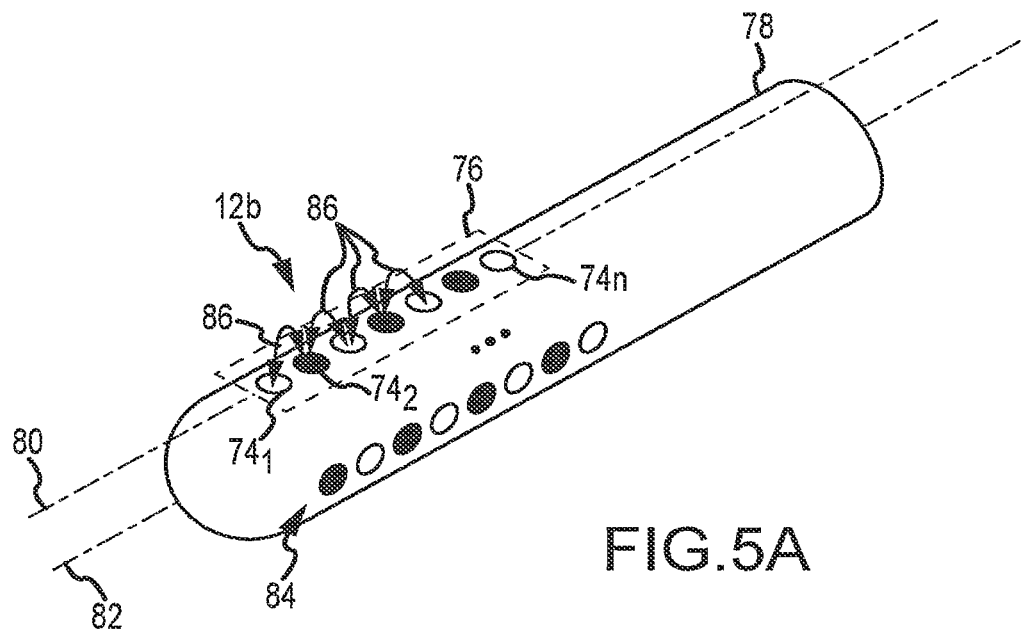
FIGS. 5A-5D and FIGS. 6-7 are isometric and plan views of direction-sensitive multi-polar electrode assemblies for creating linear lesions using bi-poles from the same electrode element line.
Figure 5B:
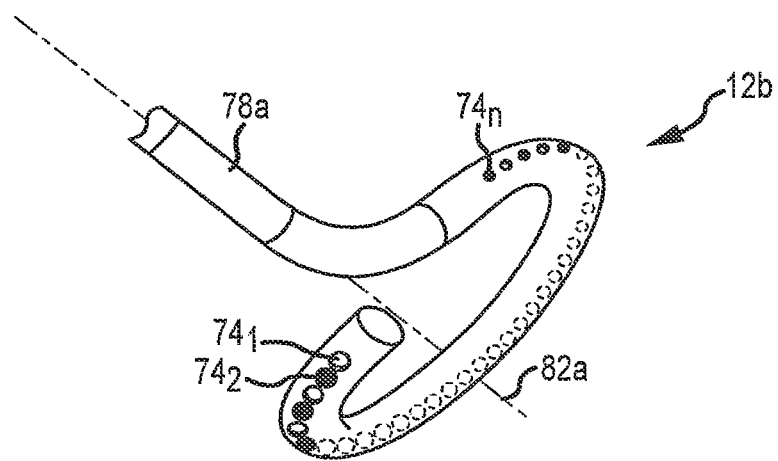
Figure 5C:
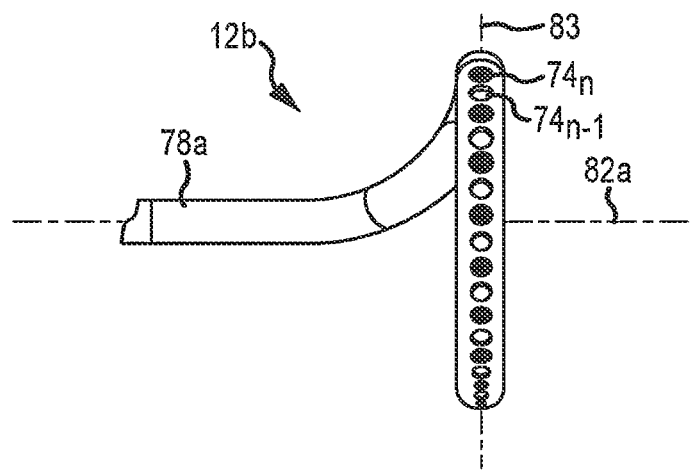
Figure 5D:
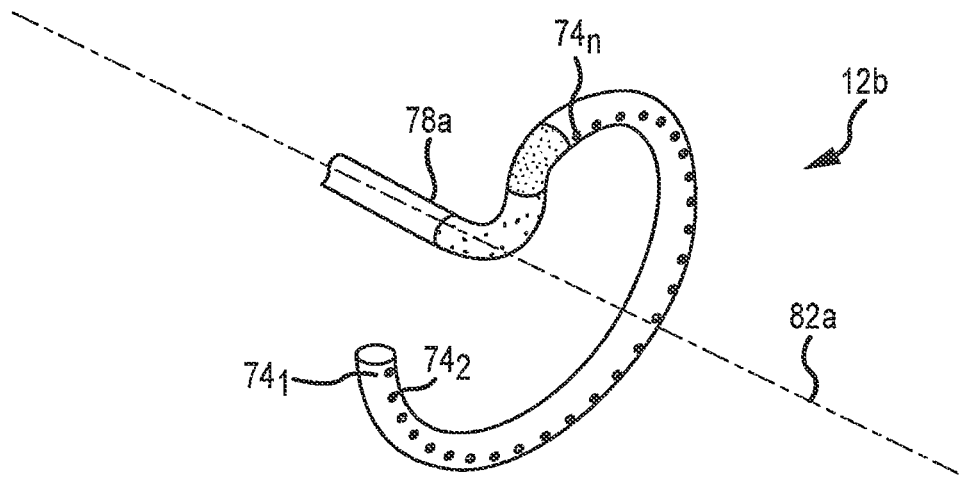
Figure 6:
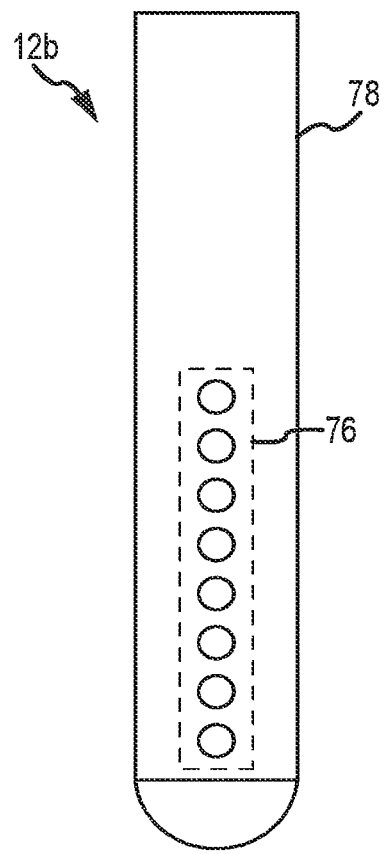
Figure 7:
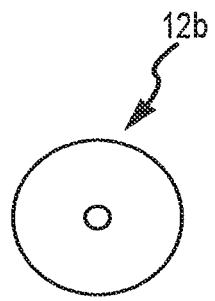

Referring to FIG. 5A, bi-poles may be formed by pairing and electrically connecting individual ones of the electrode elements (poles) $74_1$, $74_2$, ... $74_n$ taken from the same line (i.e., from the array 76 in FIG. 5A). In this instance, the electric field formed by the energization of these bi-poles is shown as field lines 86 in FIG. 5A. However, referring to FIG. 8, bi-poles may also be formed by pairing and electrically connecting individual electrode elements (poles) taken from separate, parallel arrays. In this instance, the electric field formed by the energization of these bi-poles is shown at 88 in FIG. 8. For reference, in both FIGS. 5A and 8, black electrode elements (poles) and white electrode elements (poles) may be paired to form a bipole. It should be appreciated that by using the electrode assembly 12b or 12c and forming bi-poles from one line (one array of electrode elements or poles), a narrow linear lesion may be produced. On the other hand, by using electrode assembly 12b or 12c and energizing bi-poles from two or more parallel arrays, a wider lesion may be produced. The width of the lesion will depend on the distance between the arrays (i.e., distance between the paths along with the poles in each array extend).

With reference to FIGS. 5A-10, a method will now be described using electrode assemblies 12b, 12c to create linear lesions by way of electroporation-induced primary necrosis therapy or electric field-induced apoptosis (or secondary necrosis) therapy. The first step involves maneuvering the catheter, in particular the electrode assembly thereof, to the target tissue site 16, and placing the electrode assembly 12b, 12c in contact against the tissue 16, all as already described above. The next step involves identifying which electrode elements (poles) $74_1$, $74_2$, ... , $74_n$ are in contact with the tissue 16, again as already described above, using the detector 22 and the tissue sensing circuit 24.

The next step involves energizing the identified electrode elements (i.e., those elements that are in contact with tissue) using the electroporation generator 26 in accordance with a suitable energization strategy. The energization strategy used in turn will be based on the electroporation therapy chosen. In this embodiment, the therapies include either electroporation-induced primary necrosis therapy or electric field-induced apoptosis therapy (or secondary necrosis therapy). Accordingly, the generator 26 is controlled to deliver electrical energy consistent with the electrical parameters described above to perform the selected one of these therapies. The energization strategy is preferably conducted in a bipolar fashion (i.e., electrode element to electrode element), which creates local electric fields, for example only as shown by field designated 86 (FIG. 5A) or as designated 88 (FIG. 8). The established, local electric fields are operative to create a linear lesion via electroporation-induced primary necrosis or electric field-induced secondary necrosis. As described above, the width of the legion may be controlled by energizing bipoles taken from one array of electrode elements (narrow) or by energizing bipoles taken from separate (parallel) arrays. In addition, spot lesions are also possible by selectively energizing electrodes proximal to and/or in contact with an ectopic site.

The next step involves determining whether the sought-after modification to a property of the target tissue 16 has occurred. Preferably, this step is performed using the tissue sensing circuit 24. Depending on the property sought to be modified, achieving the desired property modification can be confirmed by a physician monitoring a readout or the like of the measured or computed tissue property of interest (e.g., a read-out from the tissue sensing circuit 24 or a display in communication therewith). In an alternate embodiment, the tissue sensing circuit 24 (or other component via suitable communication) may be configured to generate a signal indicative of when the desired tissue modification has been achieved (e.g., a preset threshold). Once the desired modification to the tissue property has been achieved, the electroporation therapy with respect to the target tissue 16 may be discontinued.

With respect to FIGS. 5A-10, it should be understood that variations are possible. For example, the illustrated multi-polar electrode assemblies may comprise electrically conductive wires, rings, loops, and/or coils embedded on the surface of the catheter body (e.g., the tubular structure 78 or 78a). These embedded wires, rings, loops and/or coils may be exposed at specific sites on the catheter body to create the configurations described in those figures.

Figure 11:
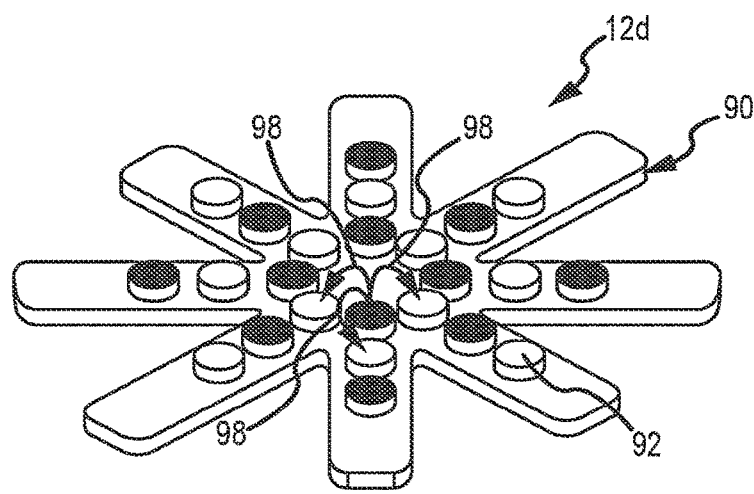
FIGS. 11-13 are isometric and plan views of a first embodiment of multi-polar multi-array electrode assembly for creating distributed or wide area lesions.
Figure 12:
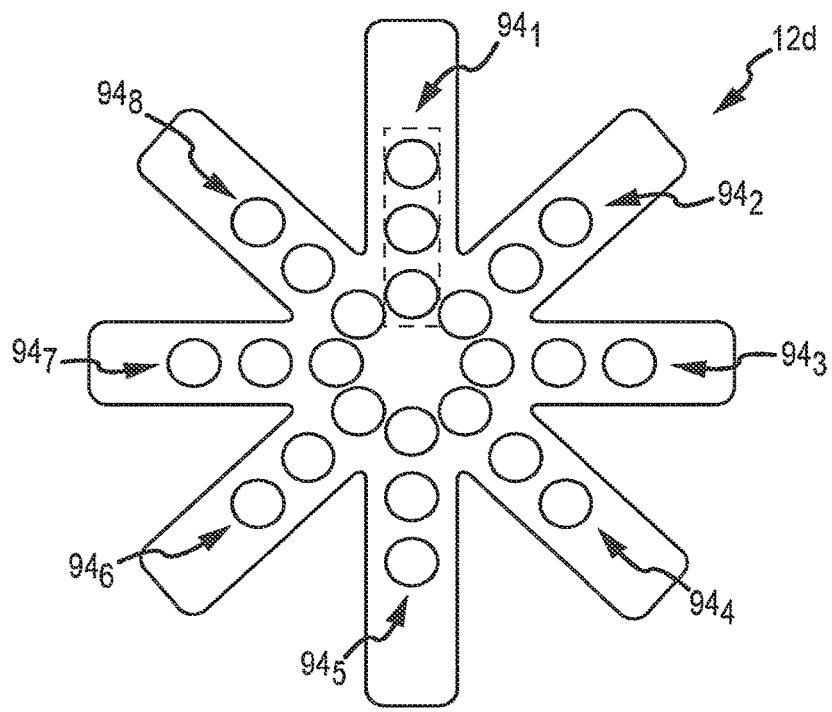
Figure 13:
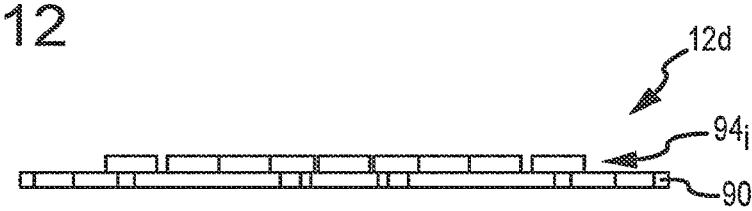

FIGS. 11-13 show a direction-sensitive multi-polar multi-array electrode assembly, designated 12d, suitable for creating distributed or wide area lesions in accordance with an electroporation therapy. Unless otherwise described below, the electrical connections and interactions of electrode assembly 12d with the components of system 10 will be the same as described above for assemblies 12a, 12b and 12c and accordingly will not be repeated.

The electrode assembly 12d is configured to be disposed at the distal end 48 of the catheter 14 and includes a base 90 comprising electrically-insulative (nonconductive) material. In the illustrative embodiment, the base 90 includes eight branches in a fan-like (asterisk-shaped) pattern. The assembly 12d further includes a plurality of electrode elements (poles) 92 arranged in a plurality of arrays (multi-array), the arrays being designated $94_1$, $94_2$, ... $94_n$ (best shown in FIG. 12) and arranged in manner corresponding to that of the base, i.e., in a fan-like pattern configured to cover a distributed or wide area for creating a corresponding lesion. The individual poles 92 may be separated from each other by intervening gaps, which may be impervious or may contain ports or pores (not shown) for irrigation purposes. In addition, in one embodiment, the separation distance between all the electrode elements (poles) may be approximately equal.

As shown in FIG. 13, the assembly 12d may be generally planar. However, the base 90 need not be planar and may alternately be configured and deployed as a pentagon array ("Pentarray"), an umbrella/parachute, an expandable/retractable loop or a balloon. Moreover, the base 90 may comprise a flex circuit configured to provide electrical connection lines between the electrode elements and the various components of the system 10.

FIGS. 14-17 show a still further embodiment of electrode assembly (designated assembly 12e) configured to be disposed at the distal end of catheter 14 where the base is configured and deployed as a plurality of expandable/retractable loops. Unless otherwise described below, the electrical connections and interactions with the components of the system 10 may be the same for assembly 12e as was set forth above for any of the electrode assemblies 12a-12d and will accordingly not be repeated.

Figure 14:
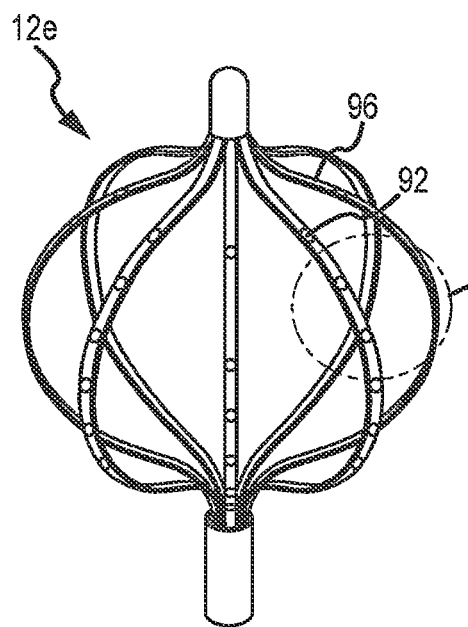
FIGS. 14-17 are isometric and plan views of a second embodiment of multi-polar multi-array electrode assembly for creating distributed or wide area lesions.

FIG. 14 is an isometric view of the assembly 14 shown in a deployed state. During insertion of the catheter 14 that includes assembly 12e, and while maneuvering the catheter 14 to the target site of the tissue 16, the assembly 14 remains in a retracted state (not shown). The electrode assembly 12e includes a plurality of loops 96 each of which carry one or more electrode elements 92. The expandable/retractable construction of assembly 12e may utilize known approaches.

Figure 15:
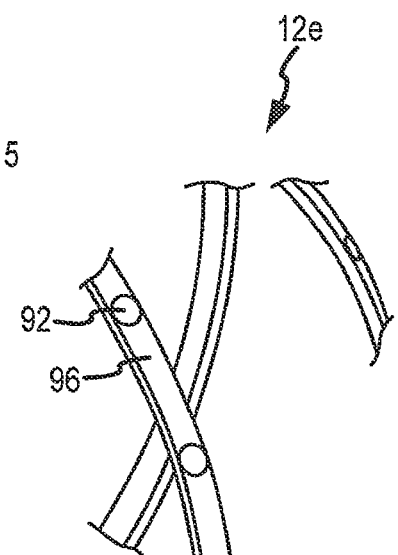
Figure 16:
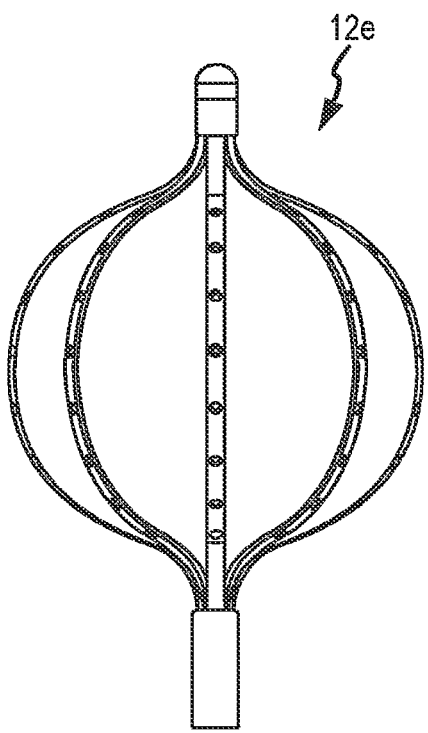
Figure 17:
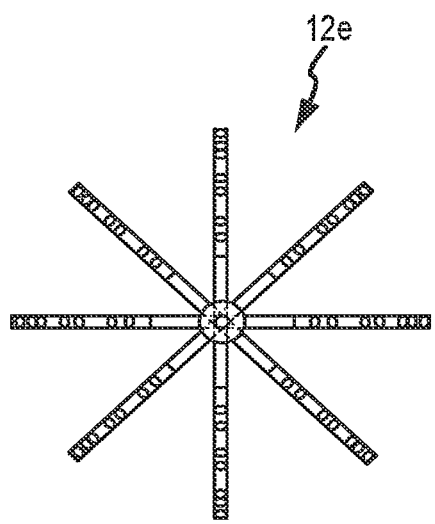

FIG. 15 is an isometric view showing, in greater detail, a portion that is encircled in FIG. 14. FIG. 16 is a side, plan view of the assembly 12e while FIG. 17 is a top, plan view of the assembly 12c.

With reference to FIGS. 11-17, a method will now be described using electrode assemblies 12d, 12e to create distributed or wide area lesions by way of electroporation-induced primary necrosis therapy or electric field-induced apoptosis (or secondary necrosis) therapy. The first step involves maneuvering the catheter, in particular the electrode assembly thereof, to the target tissue site 16, and placing the electrode assembly 12d, 12e in contact against the tissue 16, all as already described above. The next step involves identifying which electrode elements (poles) 92 are in contact with the tissue 16, again as already described above, using the detector 22 and the tissue sensing circuit 24.

The next step involves energizing the identified electrode elements (i.e., those elements that are in contact with tissue) using the electroporation generator 26 in accordance with a suitable energization strategy. The energization strategy used in turn will be based on the electroporation therapy chosen. In this embodiment, the therapies include either electroporation-induced primary necrosis therapy or electric field-induced apoptosis therapy (or secondary necrosis therapy). Accordingly, the generator 26 is controlled to deliver electrical energy consistent with the electrical parameters described above to perform the selected one of these therapies. The energization strategy is preferably conducted in a bipolar fashion (i.e., electrode element to electrode element), which creates electric fields, shown in FIG. 11 as field 98 for one exemplary electrode element (pole) to its nearest bipole neighbor elements. The electric field 98, when established using bipoles throughout the assembly 12d or 12e, is operative to create a distributed or wide area lesion via electroporation-induced primary necrosis or electric field-induced secondary necrosis.

The next step involves determining whether the sought-after modification to a property of the target tissue 16 has been effected. Preferably, this step is performed using the tissue sensing circuit 24. Depending on the property sought to be modified, achieving the desired property modification can be confirmed by a physician monitoring a readout or the like of the measured or computed tissue property of interest (e.g., a read-out from the tissue sensing circuit 24 or a display in communication therewith). In an alternate embodiment, the tissue sensing circuit 24 (or other component via suitable communication) may be configured to generate a signal indicative of when the desired tissue modification has been achieved (e.g., a preset threshold). Once the desired modification to the tissue property has been achieved, the electroporation therapy to the target tissue 16 may be discontinued.

Figure 18:
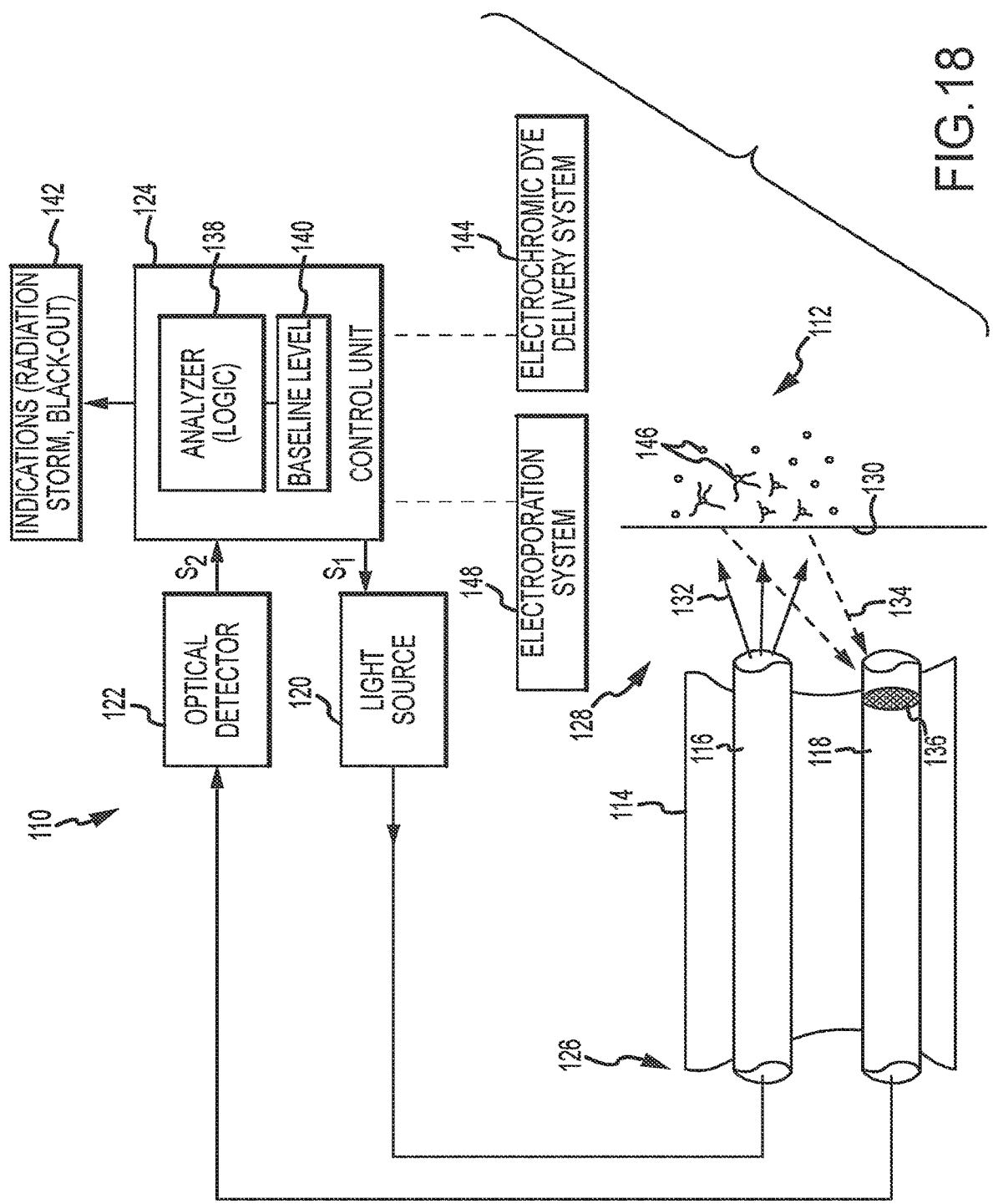
FIG. 18 is a diagrammatic and block diagram view of a system for optical-based tissue sensing for electroporation therapy.

FIG. 18 is a diagrammatic and block diagram of a system 110 for confirming the delivery and effectiveness of electroporation therapy. In the illustrative embodiment, the system 110 employs optical-based tissue sensing and is used in connection with electrochromic dyes. Electrochromic dyes will be described in greater detail below; however, generally, a property of electrochromic dyes (e.g., its color) may be controlled or modified in accordance with an electric field. This property is used by system 110. The target tissue 112 may comprise endocardial tissue within the heart of a human body. It should be understood, however, that the system 110 may find application in connection with a variety of tissues within human and non-human bodies.

A method for confirming the delivery and effectiveness of electroporation generally includes a number of steps. The first step involves applying the electrochromic dyes to the target tissue. The next step involves optically monitoring the dyes to establish a baseline optical characteristic. The next step involves applying an electric field in the vicinity of the tissue in accordance with an selected electroporation energization strategy. Finally, the method involves detecting changes in the monitored optical characteristic (e.g., of the tissue site after the dye has been delivered). For example, an intense color change can be indicative of an effective electric field or an "optical black out" can be indicative of a successful conclusion of electroporation therapy. These steps will be described in greater detail below, along with a description of suitable system components for performing the method.

The system 110 includes a mechanism suitable for use in a catheter that may be used to carry light to and from the tissue 112, and to analyze the light captured at the tissue site. In this regard, the system 110 includes a deformable, tubular body 114 (e.g., a catheter), a plurality of optic fibers including fibers 116, 118, an electromagnetic radiation source 120 (i.e., light source), an electromagnetic radiation sensor 122 (i.e., optical detector) and a control unit 124 (e.g., an electronic control unit (ECU)).

The body 114 functions as a catheter and is provided to house fibers 116, 118 for example as seen by reference to PCT International Application PCT/US09/39367 filed Apr. 2, 2009, published WO 2009/124220 on Oct. 8, 2009 entitled "PHOTODYNAMIC-BASED MYOCARDIAL MAPPING DEVICE AND METHOD", owned by the common assignee of the present invention and hereby incorporated by reference in its entirety. The body 114 may also allow removal of bodily fluids or injection of fluids and medicine into the body. The body 114 may further provide a means for transporting surgical tools or instruments within a body. For example, the body 114 may house an electrode (not shown) used in ablation of the tissue 112. The body 114 may be formed from conventional materials such as polyurethane. The body 114 is tubular and is deformable and may be guided within a body by a guide wire or other means known in the art. The body 114 has a proximal end 126 and a distal end 128 (as used herein, "proximal" refers to a direction toward the body of a patient and away from the clinician while "distal" refers to a direction toward the clinician and away from the body of a patient). The body 114 may be inserted within a vessel located near the surface of a patient (e.g., in an artery or vein in the leg, neck, or arm) in a conventional manner and maneuvered to a region of interest 130 in the tissue 112.

The optic fibers 116, 118 are provided to transmit and receive electromagnetic radiation. The fibers 116, 118 are conventional and may be made from various glass compositions (e.g., silica) or plastics (e.g., polymethyl methaacrylate (PMMA) surrounded by fluorinated polymers). The fibers 116, 118 include a core and a cladding with the core having a higher refractive index than the cladding. The fibers 116, 118 may further include a buffer layer and a jacket as is known in the art. The fibers 116, 118 may, for example, comprise any of a variety of common fibers sold by Polymicro Technologies, Inc., Edmund Optics, Inc., Keyence Corporation, or Mitsubishi International Corporation. The fibers 116, 118 are disposed within the catheter body 114 and may extend from the proximal end 126 to the distal end 128.

The electromagnetic radiation source 120 is provided to generate a first set of electromagnetic radiation for transmission through one or more optic fibers (i.e., a first light signal). In the illustrated embodiment, the source 120 transmits radiation through the fiber 116. The source 20 may comprise, for example, a light emitting diode (LED) or laser (e.g., a laser diode). The source 120 may produce a monochromatic or spectral radiation and the radiation may be polarized or unpolarized. The source 120 may generate radiation at various points along the electromagnetic spectrum including, for example, visible light, infrared, near infrared, ultraviolet and near ultraviolet radiation. The radiation source 120 may emit radiation in a controlled manner responsive to signals $S_1$ received from the control unit 124. The source 120 may be located at or near the proximal end of fiber 116 and/or proximal end 126 of the catheter body 114. The source 120 may produce both radiation for diagnostic and ablative purposes, or only for one purpose. Multiple sources may also be used, either in conjunction with the same fibers or different fibers.

The electromagnetic radiation sensor 122 (i.e., optical detector) is provided to generate a signal $S_2$ in response to a second set of electromagnetic radiation (i.e., a second light signal) received through an optic fiber. In the embodiment illustrated in FIG. 18, the sensor 122 receives radiation transmitted through fiber 118. Radiation received through the fiber 118 originates from the tissue 112 in response to radiation transmitted through the fiber 116 from the source 120. The sensor 122 may comprise a photodiode. The sensor 122 may be located at or near the proximal end of fiber 118 and/or proximal end 126 of the catheter body 114.

The control unit 124 generates one or more signals, designated $S_1$, to selectively activate the source 120. In response, the source 120 generates a set of electromagnetic radiation (illustrated generally in FIG. 1 by solid arrows 132) that is transmitted through and out of the fiber 116 and projected toward and therefore incident upon the region of interest 130 of the tissue 12. Another set of electromagnetic radiation (illustrated generally in FIG. 1 by broken line arrows 134) originates at the tissue 12 in response to the radiation 132 transmitted through fiber 116, particularly altered by the presence of the electrochromic dyes. The radiation 134 originating from tissue 112 may comprise at least a portion of radiation 132 reflected by the tissue 112. In alternate embodiments, a filter 136 may be disposed within the return fiber 118 or may cover the proximal or distal end of the fiber 118 to control the passage of radiation 134 to the sensor 122 by permitting passage of radiation of a selected wavelength (or range of wavelengths) while filtering out radiation 132 and optical noise. Other variations are possible, including the use of a lens and/or other light modifying structures. Other embodiments suitable for carrying light to and from the tissue site are known in the art, for example as seen by reference to PCT International Application WO/US08/87426 filed Dec. 18, 2008 entitled "PHOTODYNAMIC-BASED TISSUE SENSING DEVICE AND METHOD", owned by the common assignee of the present invention and hereby incorporated by reference in its entirety.

The control unit 124 provides a means for selectively activating source 120 to direct a set of electromagnetic radiation through the fiber 116 to the tissue 112. The control unit 124 also provides a means for receiving a signal $S_2$ generated by the sensor 122 in response to another set of electromagnetic radiation received through the fiber 118 and originating from or acquired at the region of interest 130 of the tissue 112 in response to the radiation transmitted through fiber 116. The control unit 124 also provides a means 138 for analyzing the detected signal $S_2$ to assess the changes (if any) in the electrochromic dyes indicative of whether the electroporation therapy to the tissue 112 has been effective or not. Among other things, the analyzer 138 establishes a baseline optical characteristic 140 before the electroporation therapy has begun to provide a foundation against which changes can be determined and assessed. The optical characteristic 140 is the result of the analysis of the signal output from the sensor 122 and may correspond to one or more characteristics of the returned light signal 134. The control unit 124 may be further configured to output indications 142, including at least a first indication during electroporation therapy that the energizing strategy is producing an adequate electric field at the tissue site, and a second indication when the electroporation therapy has been carried on sufficiently to be deemed effective (i.e., complete). The logic performed by the analyzer 138 in making the assessments will be described in greater detail below.

The control unit 124 may comprise a programmable microprocessor or microcontroller or may comprise an application specific integrated circuit (ASIC). The control unit 124 may include a central processing unit (CPU) and an input/output (I/O) interface through which the control unit 124 may receive a plurality of input signals including signals generated by sensor 122 and generate a plurality of output signals to convey information regarding characteristics of the tissue 112 (more particularly, characteristics of the second light signal acquired at the tissue site, from which various conclusions may be drawn, as described herein). Alternatively, signals may be transmitted wirelessly in a conventional manner.

Embodiments of the system 110 also include a means or a system 144 for delivering electrochromic dye 146 to the tissue 112. Electrochromic dyes change color in response to changes in the electric field. The dye may also be capable of ablating the tissue. Embodiments make use of this property to monitor the progress and ultimate success of electroporation therapy. Examples of suitable electrochromic dyes includes fast-acting dyes, such as an electrochromic and potentiometric dye such as di-4-ANEPPS and di-4-ANEPPQ, belonging to a structural class called styryl or naphthylstyryl. Certain electrochromic dyes are known for use in optical mapping applications.

Dye 146 may be applied to the tissue 112 in a variety of ways. For example, the dye 146 may be introduced locally (i.e., through in-situ delivery) or systemically (i.e., such as through injection into the coronary artery). It should be understood that the system and method may also involve use of multiple electrochromic dyes 146.

Embodiments of the system 110 also include an electroporation system 148 for providing a catheter-based device configured to establish an electric field sufficient to cause electroporation in the tissue 112. In general, the system 148 includes electroporation electrodes at a distal end of the catheter and an electroporation generator configured to energize the electroporation electrodes in accordance with an electroporation energizing strategy. For example, any of the embodiments of FIG. 1-17 described above may be used to conduct the desired electroporation therapy, as well as other configurations known in the art, as seen by reference to U.S. Patent Publication 2009/0171343, application Ser. No. 11/968,044 filed Dec. 31, 2007 entitled "PRESSURE-SENSITIVE FLEXIBLE POLYMER BIPOLAR ELECTRODE", assigned to the common assignee of the present invention, and hereby incorporated by reference in its entirety.

Figure 19:
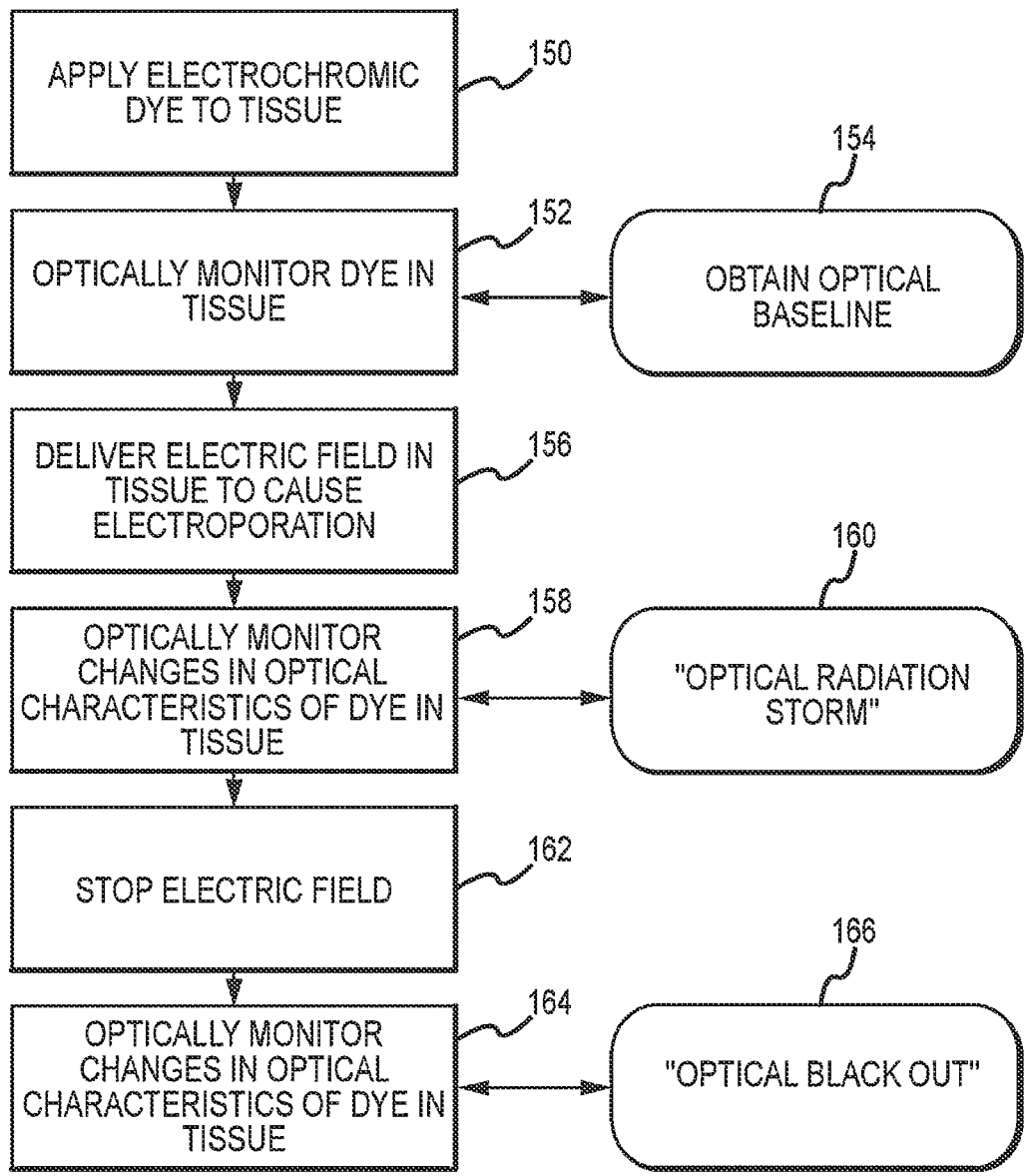
FIG. 19 is flowchart of a method for optical-based tissue sensing for electroporation therapy.

FIG. 19 is flowchart of a method for optical-based tissue sensing to confirm the progress of and successful completion of electroporation therapy. The method begins in step 150.

In step 150, the electrochromic dyes 146, as described above, are applied to the tissue 112, in any of the ways set forth above. The method proceeds to step 152.

In step 152, the control unit 124 generates the control signal $S_1$ to activate the light source 120 to irradiate the tissue 112 with electromagnetic radiation (light) 132. At the same time (i.e., at a first time after the dye has been applied but before an electric field has been applied to the tissue), the control unit 124 monitors (e.g., samples) the signal $S_2$ generated by the light detector 122. The analyzer 136 assesses the samples of the signal $S_2$, which is indicative of the light 134 picked up at the distal end of the optic fiber 118, to establish a first, baseline optical characteristic (step 154) of the electrochromic dye at the tissue site 112. It should be appreciated that the return light signal 134 is dye-mediated. In one embodiment, the optical characteristic(s) assessed include a light intensity and a spectral assessment (i.e., color) of the light signal 134 acquired at tissue 112. In other words, the analyzer 138 measures and records the baseline light intensity and optionally color or other spectral signature (see block 140 in FIG. 18). The analyzer 138 will use this baseline optical characteristic stored in block 140 to make subsequent assessments.

In step 156, the electroporation system 148 is operative to energize the electroporation electrodes (not shown in FIG. 18) in accordance with an electroporation energizing strategy to establish an electric field in the vicinity of the tissue 112. The method proceeds to step 158.

In step 158, the analyzer 138 continues to monitor the signal S2 output from the sensor 122, which as described above corresponds to the light signal 134 acquired at the tissue site 112. As described in the Background, an obstacle to the use of electroporation therapy for certain therapeutic applications involves the time lag in confirming the success of the therapy. In accordance with the invention, the analyzer 138 is configured to continue to monitor the signal S2 while the electric field is being applied even after the baseline optical characteristic has been set. During application of the electric field as typically used to effect electroporation, the electrochromic dye will exhibit an "optical radiation storm" of intense color change. This is because the subject dyes change emission proportional to the voltage across them, which in this case is the cell depolarization voltage since the dyes bind to the membrane. Embodiments of the invention may use this "optical radiation storm" as an indicator/monitor of the in situ strength of the electric field on the cell membrane during the electroporation therapy. Accordingly, the analyzer 138 is configured to monitor the optical detector output signal S2 looking for an optical characteristic representative of an "optical radiation storm". In an embodiment, the analyzer 138 is configured to detect a color change (e.g., through spectral/wavelength analysis), and more specifically, in a preferred embodiment, a color change compared to the baseline (i.e., with the cells at rest). It should be further understood that the once a particular dye has been selected, its color shift (e.g., to red or violet) will be known and thus can be anticipated by the analyzer logic 38 (i.e., can be configured to look specifically for a spectral component). It should be further understood that while the dye itself exhibits a color shift, perhaps to a particular part of the spectrum in some embodiments, that the dye color may be distinct from the display color used to represent the tissue to the physician (i.e., on a display screen). In this regard, while information indicative of the dye color may be captured using a light-to-voltage converter, the color or mode of the display of this information is independent. This is shown in step 160 (i.e., see step 160—detection of the "optical radiation storm").

In one embodiment, the "optical radiation storm" is detected based on a change in color of the light 134 (as represented by signal $S_2$) relative to the color of the baseline optical characteristic recorded before the electric field was applied. In another embodiment, the color of the optical radiation storm is known ahead of time, and the analyzer 138 may be configured to detect such a condition, even without comparison to the color/spectrum of the baseline reading.

The analyzer 138 is further configured to output a suitable indication (sec block 142 in FIG. 18) when it detects the "optical radiation storm" (i.e., indicative of adequate electric field strength for electroporation on the cell membrane). The method proceeds to step 162, where the electroporation system 148 de-energizes the electroporation electrodes (not shown) that were used to create the electric field, thereby discontinuing the electric field. The method proceeds to step 164.

Alternately, however, in FIG. 19, the step (or block) 164 may be above or in other words precede step (or block) 162. This ordering may be used because typically the method may dictate that the electric field be stopped after, or in response to, the detection of the "Optical Black Out." (block 166).

In step 164, the analyzer 138 continues to monitor the optical detector output signal $S_2$. An efficacious electroporation is expected to cause the electrochromic dyes to be removed from the surface of the cell membrane, thereby resulting in a "black out" of the dye-mediated optical signal from the target tissue 112 (i.e., the light signal 134). This "black out" may be used by the system 110 (analyzer 138 in particular) as a confirmation of the efficacy of electroporation in the target tissue 112. Accordingly, the analyzer 138 in step 164 is configured to continue to monitor signal $S_2$ for an "optical black out" (step 166). In an embodiment, the analyzer 138 is configured to assess the light intensity level represented in the monitored signal $S_2$ relative to the light intensity level represented in the baseline optical characteristic. When the light intensity level has been reduced by at least a predetermined amount (i.e., "black out"), then the analyzer 138 produces an output indication (see block 142 FIG. 18), which may include a confirmation of the efficacy of the electroporation therapy.

FIGS. 20-21 show fiber optic temperature sensing electrode systems in first and second embodiments. Generally, temperature sensing is achieved by using thermochromic or thermotropic materials, such as a temperature sensitive dye, polymers or hydrogels, that change color in response to changes in temperature. For example, a thermochromic solution of $CoCl_2 \cdot 6H_2O$ may be used as a temperature sensing material. The use of the these materials overcomes the problems described in the Background pertaining to temperature sensing errors due to location eccentricity of thermocouples or thermistors.

FIG. 20 is a combined partial cross-sectional and block diagram of a fiber optic temperature sensing electrode system 170 comprising a plurality of proximal-side components collectively designated 172 and an electrode catheter in a first embodiment designated 174a. A first light signal transmitted to the electrode catheter 174a and a second light signal returning to the proximal-side components are shown in a composite manner by the double arrow-headed line 176.

The electrode catheter 174a includes a shaft 178 having a proximal end 180 and a distal end 182. The shaft 178 may be of conventional construction and materials, such as that described above in connection with FIG. 18.

The catheter 174a further includes an electrode 184 at the distal end 182. The electrode 184 includes a main body portion having an outer surface 186 and an inner cavity 188 defined by an inner surface 190. The electrode 184 may comprise conventional electrically-conductive materials, such as described above in connection with FIGS. 2-4 for example. It should understood, however, that other electrode construction approaches and materials may be used. For example, the electrode 184 may alternatively comprise an electrically-conductive electrode configured for use in irrigated-electrode application, a flexible polymer electrode or a fiber optic electrode.

At least a portion of the inner surface 190 comprises a thermally-sensitive material 192 configured to change color as a function of temperature, such as thermochromic or thermotropic materials. In FIG. 20, the material 192 is shown as a series of "o" symbols distributed along the inner surface 190. In one embodiment, the material 192 may be impregnated into the inner surface of the electrode 184. In an alternate embodiment, the material 192 may be applied as a thin coating to the inner surface 192 of the electrode 184.

FIG. 21 shows another embodiment of the catheter for use in system 170, designated electrode catheter 174b. The catheter 174b differs with respect to the catheter 174a of FIG. 20 in that the optic fiber includes a lumen at its distal end that is at least partially filled with the material 192, rather than the material 192 being either impregnated or applied as a thin layer as in FIG. 21. The system 170 of FIG. 21 may otherwise in all respects be the same as the system of FIG. 20.

The catheter 174a further includes at least one optic fiber 194 in the shaft 178 extending between the proximal and distal ends 180, 182. The optic fiber 194 includes proximal and distal ends 196, 198 as well. The distal end 198 of the optic fiber 194 is in optical communication with the material 192 (e.g., in optical communication with the cavity, the inner surface thereof or a lumen having or containing the material 192 as in FIG. 21). In this regard, the optic fiber 194 may have its distal end 198 finished or otherwise provided with a lens or other structure to facilitate acquisition of a light signal in accordance with conventional approaches. The optic fiber 194 may be of conventional construction and materials, such as for example as described above in connection with FIG. 18.

The proximal-side components 172 include a light source 200, an optical detector 202 generating an output signal 204, a control unit 206 (e.g., an electronic control unit (ECU)) having an analyzer portion 208, a storage mechanism 210 for storing predetermined spectrum-versus-temperature calibration data and an output block 212, which may comprise a temperature signal indicative of a temperature of the electrode 184.

The light source 200 is configured to generate a first light signal. The proximal end 196 of the optic fiber 194 is configured to interface with the light source 200 and carry the first light signal to its distal end 198, where the first light signal is projected onto and is incident upon at least the thermally-sensitive material 192. The distal end 198 of the optic fiber 194 is further configured to acquire a second light signal that is reflected, refracted or is otherwise available within the cavity 188. The optic fiber 194 is further configured to transmit the second light signal acquired at its distal end 198 to its proximal end 196. The optical detector 202 is optically coupled to the distal end 198 and is configured to detect the second light signal and generate the output signal 204. The light source 200 and the optical detector 202 may comprise conventional components, such as those described above in connection with FIG. 18.

The analyzer 208 of the control unit 206 is configured to assess the detector output signal 204 and generate a temperature signal 212 representative of the temperature of the electrode 184. In an embodiment, the analyzer 208 is configured to use predetermined calibration data 210, which may comprise data that correlates the spectrum (i.e., a wavelength-intensity curve) of the received light as represented by output signal 204 with a corresponding temperature. It should be understood that the calibration data 210 will be tailored to suit the characteristics of the material 192, with the foregoing being exemplary only and not limiting in nature. The control unit 206 may comprise conventional components, as described above in connection with FIG. 18, subject to being specially-configured by way of analyzer 208 to perform the functions described herein. In sum, the thermochromic material serves as a temperature-to-light converter while the optical detector serves as the light-to-voltage converter. The analyzer 208 evaluates the voltage signal 204 based on the conversion relationships determined to faithfully take into account the temperature-to-light and light-to-voltage conversion processes to produce an indication of sensed temperature. The calibration data 210 may be used to adjust the conversion relationships to any variations in the temperature-to-light and light-to-voltage conversion processes. In an embodiment, the calibration data 210 may updated from time to time to take into account changes in the temperature-to-light and light-to-voltage conversion processes that may occur over time.

Through the foregoing, temperature sensing errors may be avoided. In addition, the optic fiber is immune to radiofrequency interference (RFI) and electromagnetic interference (EMI), and accordingly embodiments consistent with the invention may likewise exhibit such immunity.

The embodiments described herein enable a variety of applications of electroporation therapy, including the ability (1) to modulate tissue properties, such as (i) electrical conductivity of the tissue in order to make the tissue more responsive/irresponsive to RF ablation, and/or (ii) chemical/electrochemical properties of the tissue in order to make the tissue more responsive/irresponsive to photodynamic based tissue sensing and/or ablation, and/or (iii) acoustic properties of the tissue in order to make the tissue responsive/irresponsive to ultrasound based tissue sensing and/or ablation; and/or (2) to confirm the target tissue (such as an ectopic site); and/or (3) to prevent stenosis.

It should be understood that the various control units, computer systems and the like described herein may include conventional processing apparatus known in the art (i.e., both hardware and/or software), including the capability of executing pre-programmed instructions stored in an associated memory, all performing in accordance with the functionality described herein. It is contemplated that the methods described herein, including without limitation the method steps of embodiments of the invention, may be programmed in a preferred embodiment, with the resulting software being stored in an associated memory and may also constitute the means for performing such methods. Implementation of embodiments, in software, in view of the foregoing enabling description, would require no more than routine application of programming skills by one of ordinary skill in the art. The system may further be of the type having both ROM, RAM, a combination of non-volatile and volatile (modifiable) memory so that the software can be stored and yet allow storage and processing of dynamically produced data and/or signals. Moreover, an article of manufacture in accordance with embodiments of the invention includes a computer-readable storage medium having a computer program encoded thereon for performing the methods described in this application. The computer program includes code that, when executed by a computer, causes the computer to perform the steps of the methods described herein.

Although numerous embodiments of this invention have been described above with a certain degree of particularity, those skilled in the art could make numerous alterations to the disclosed embodiments without departing from the spirit or scope of this invention. All directional references (e.g., plus, minus, upper, lower, upward, downward, left, right, leftward, rightward, top, bottom, above, below, vertical, horizontal, clockwise, and counterclockwise) are only used for identification purposes to aid the reader's understanding of the present invention, and do not create limitations, particularly as to the position, orientation, or use of the invention. Joinder references (e.g., attached, coupled, connected, and the like) are to be construed broadly and may include intermediate members between a connection of elements and relative movement between elements. As such, joinder references do not necessarily infer that two elements are directly connected and in fixed relation to each other. It is intended that all matter contained in the above description or shown in the accompanying drawings shall be interpreted as illustrative only and not limiting. Changes in detail or structure may be made without departing from the spirit of the invention as defined in the appended claims.

What is claimed is:

1. An electroporation catheter assembly comprising:
   a handle;
   a shaft comprising a proximal end and a distal end, wherein the proximal end of the shaft is coupled to the handle; and
   an electrode assembly positioned at the distal end of the shaft, the electrode assembly comprising a plurality of loops and a plurality of electrodes, each loop comprising at least one electrode of the plurality of electrodes, wherein each of the plurality of electrodes is configured to be selectively energized to produce a lesion in tissue, wherein the plurality of loops are selectively transitionable between a retracted state and an expanded state, and wherein the plurality of electrodes are configured to be selectively energized in a bipolar fashion to deliver electrical energy sufficient to cause irreversible electroporation between i) a first electrode on a first loop of the plurality of loops and ii) a second electrode on a second, different loop of the plurality of loops.

2. The electroporation catheter assembly of claim 1, wherein the plurality of loops comprises at least five loops.

3. The electroporation catheter assembly of claim 1, wherein each loop comprises at least four electrodes.

4. The electroporation catheter assembly of claim 1, wherein the plurality of loops form a basket shape in the expanded state.

5. The electroporation catheter assembly of claim 1, wherein each loop of the plurality of loops extends between a loop proximal end and a loop distal end.

6. The electroporation catheter assembly of claim 1, wherein each of the plurality of electrodes is configured to sense an electrical characteristic to facilitate determining whether that electrode is in contact with the tissue.

7. The electroporation catheter assembly of claim 6, wherein the electrical characteristic is an impedance.

8. An electroporation system comprising:
   an electroporation generator; and
   a catheter coupled to the electroporation generator, the catheter comprising:
      a handle;
      a shaft comprising a proximal end and a distal end, wherein the proximal end of the shaft is coupled to the handle; and
      an electrode assembly positioned at the distal end of the shaft, the electrode assembly comprising a plurality of loops and a plurality of electrodes, each loop comprising at least one electrode of the plurality of electrodes, wherein each of the plurality of electrodes is configured to be selectively deliver energy generated by the electroporation generator to produce a lesion in tissue, wherein the plurality of loops are selectively transitionable between a retracted state and an expanded state, and wherein the plurality of electrodes are configured to be selectively energized in a bipolar fashion to deliver electrical energy sufficient to cause irreversible electroporation between i) a first electrode on a first loop of the plurality of loops and ii) a second electrode on a second, different loop of the plurality of loops.

9. The electroporation system of claim 8, wherein the plurality of loops comprises at least five loops.

10. The electroporation system of claim 8, wherein each loop comprises at least four electrodes.

11. The electroporation system of claim 8, wherein the plurality of loops form a basket shape in the expanded state.

12. The electroporation system of claim 8, wherein each loop of the plurality of loops extends between a loop proximal end and a loop distal end.

13. The electroporation system of claim 8, wherein each of the plurality of electrodes is configured to sense an electrical characteristic to facilitate determining whether that electrode is in contact with the tissue.

14. The electroporation system of claim 13, wherein the electrical characteristic is an impedance.

15. The electroporation system of claim 13, further comprising a detector coupled to the catheter, the detector configured to determine which electrodes of the plurality of electrodes are in contact with the tissue based on the sensed electrical characteristic.

16. A method of operating an electroporation system, the method comprising:
   coupling an electroporation generator to a catheter, the catheter including a handle, a shaft including a proximal end and a distal end, wherein the proximal end of the shaft is coupled to the handle, and an electrode assembly positioned at the distal end of the shaft, the electrode assembly including a plurality of loops and a plurality of electrodes, each loop including at least one electrode of the plurality of electrodes, wherein the plurality of loops are selectively transitionable between a retracted state and an expanded state;

selectively delivering energy generated by the electroporation generator and sufficient to cause irreversible electroporation between i) a first electrode on a first loop of the plurality of loops and ii) a second electrode on a second, different loop of the plurality of loops to produce a lesion in tissue.

17. The method of claim 16, further comprising:

sensing an electrical characteristic at at least one electrode of the plurality of electrodes; and determining, using a detector coupled to the catheter, whether the at least one electrode is in contact with the tissue based on the sensed electrical characteristic.

18. The method of claim 17, wherein the electrical characteristic is an impedance.

* * * * *